US011497678B2

(12) United States Patent
Sifferlin

(10) Patent No.: US 11,497,678 B2
(45) Date of Patent: Nov. 15, 2022

(54) SYSTEM AND METHOD FOR AIRWAY MANAGEMENT

(71) Applicant: Sifferlin Conceptual Designs Company, LLC, Wooster, OH (US)

(72) Inventor: Daniel J. Sifferlin, Wooster, OH (US)

(73) Assignee: Sifferlin Conceptual Designs Company, LLC, Wooster, OH (US)

( * ) Notice: Subject to any disclaimer, the term of this patent is extended or adjusted under 35 U.S.C. 154(b) by 728 days.

(21) Appl. No.: 16/574,288

(22) Filed: Sep. 18, 2019

(65) Prior Publication Data

US 2021/0077345 A1 Mar. 18, 2021

(51) Int. Cl.
*A61F 5/56* (2006.01)
*A61H 31/00* (2006.01)

(52) U.S. Cl.
CPC ... *A61H 31/008* (2013.01); *A61H 2201/1607* (2013.01); *A61H 2201/1619* (2013.01); *A61H 2201/1676* (2013.01); *A61H 2205/026* (2013.01)

(58) Field of Classification Search
CPC ............ A61H 31/008; A61H 2205/026; A61H 1/0296; A61H 2201/1609; A61H 2205/04; A61G 13/12; A61G 13/121; A61G 13/1215; A61G 7/072; A61F 5/055; A61F 5/3707; A47G 9/1081
See application file for complete search history.

(56) References Cited

U.S. PATENT DOCUMENTS

| | | | | |
|---|---|---|---|---|
| 4,782,824 A * | 11/1988 | Davies | A61F 5/055 | 602/18 |
| 6,171,314 B1 * | 1/2001 | Rotramel | A61F 5/05891 | 602/18 |
| 6,625,829 B2 * | 9/2003 | Zell | A61F 5/055 | 5/636 |
| 6,969,366 B1 * | 11/2005 | Reddick | A61B 90/18 | 602/18 |
| 7,096,869 B1 * | 8/2006 | Orlewicz | A61F 5/3707 | 128/845 |
| 7,406,732 B2 * | 8/2008 | Ramaiah | A61G 13/12 | 5/636 |
| 8,950,027 B2 * | 2/2015 | Yamamoto | A61F 5/055 | 5/636 |
| 9,808,370 B1 * | 11/2017 | Reser | A47G 9/1081 | |
| 10,881,226 B1 * | 1/2021 | Ou | A47G 9/10 | |
| 2003/0070684 A1 * | 4/2003 | Saied | A61M 16/0497 | 128/869 |
| 2008/0163875 A1 * | 7/2008 | Aarestad | A61F 5/56 | 128/846 |
| 2009/0095309 A1 * | 4/2009 | Derrick | A61F 5/3707 | 128/870 |
| 2010/0224198 A1 * | 9/2010 | Ayuse | A61F 5/56 | 128/848 |

(Continued)

*Primary Examiner* — Justine R Yu
*Assistant Examiner* — Christopher E Miller
(74) *Attorney, Agent, or Firm* — Sand, Sebolt & Wernow Co., LPA

(57) ABSTRACT

Systems and methods for airway management are provided. The airway management devices may be configured to align the oropharyngeal, laryngeal and tracheal axes of a person's head and/or support a neck region and chin and posterior mandibular region of a person. The airway management devices may provide forces similar to forces provided by a conventional head tilt chin lift maneuver and a conventional jaw thrust maneuver.

16 Claims, 26 Drawing Sheets

(56) References Cited

U.S. PATENT DOCUMENTS

| | | | | |
|---|---|---|---|---|
| 2011/0036355 | A1* | 2/2011 | Farnum | A61G 13/1215<br>128/845 |
| 2013/0221168 | A1* | 8/2013 | Bernardoni | A47C 16/00<br>248/118 |
| 2016/0066697 | A1* | 3/2016 | Adams | A47G 9/109<br>5/636 |
| 2016/0184127 | A1* | 6/2016 | Shinzato | A61F 5/56<br>128/848 |
| 2021/0227980 | A1* | 7/2021 | Lobo | A47G 9/109 |
| 2021/0235900 | A1* | 8/2021 | Choi | A47G 9/1009 |
| 2022/0054300 | A1* | 2/2022 | Vaidya | A61F 5/56 |

* cited by examiner

SYSTEM AND METHOD FOR AIRWAY MANAGEMENT

CROSS REFERENCE TO RELATED APPLICATIONS

This application claims the benefit of U.S. Provisional Application Ser. No. 62/733,301, filed on Sep. 19, 2018; the disclosure of which is incorporated herein by reference.

TECHNICAL FIELD

The present disclosure relates generally to airway management devices. More particularly, the present disclosure relates to airway management devices that restore and/or maintain a patent airway of a person and/or support various portions of a person's head region and neck region. Specifically, the present disclosure relates to airway management devices configured to align the oropharyngeal, laryngeal and tracheal axes of a person's head and/or support a neck region and chin and posterior mandibular region of a person.

BACKGROUND

Generally, Monitored Anesthesia Care (MAC) and regional anesthesia are commonly used anesthetic techniques that utilize local anesthesia together with sedation and analgesia. MAC is often used in combination with regional anesthesia such as spinals, epidurals, and peripheral nerve blocks. One risk associated with using MAC anesthesia and sedation on a patient is that the airway of the patient may become obstructed which may lead to, inter alia, respiratory depression, hypoxia or hypercarbia. Hypoxia which is a deficiency in the amount of oxygen reaching the tissues. Hypercarbia which is a condition of abnormally elevated carbon dioxide ($CO_2$) levels in the blood.

An airway obstruction typically occurs due to a loss of tonicity of the submandibular muscles. The submandibular muscles provide direct support of the tongue and indirect support of the epiglottis. As a result of the loss of tonicity, posterior displacement of the tongue may occur and the tongue then occludes the airway at the level of the pharynx. One conventional technique for opening an obstructed airway is a head tilt chin lift maneuver. This procedure is used to prevent the tongue from obstructing the upper airways. The maneuver is performed by tilting the head backwards in unconscious patients, often by applying pressure to the forehead and the chin. One drawback associated with this technique is that the person typically needs to use one or two hand techniques to perform this maneuver and this prevents the person from performing other important tasks related to assisting the patient in distress.

Another conventional technique for opening an obstructed airway is a jaw thrust maneuver. This procedure is typically used on a supine patient, i.e., a patient laying on his or her back. The jaw thrust maneuver is performed by a person using index and middle fingers to physically push the posterior portions of the lower jaw of a patient, i.e., the jaw portions below the ear, upwards while their thumbs push down on the chin to open the mouth. When the mandible, i.e., lower jaw, is displaced forward, the mandible pulls the tongue forward and prevents the tongue from obstructing the entrance to the trachea. One drawback associated with this technique is that a person typically needs to use one or two hands to perform the maneuver which, again, prevents the person from performing other important tasks.

Additionally, a percentage of the population suffers from weakened shoulder and neck muscles. This may cause an individual to struggle to maintain their head and neck in an upright position and can result in pain or discomfort for the afflicted individual. In some instances, the inability to hold their head and neck in an upright position can result in some obstruction of the airways.

SUMMARY

The inventor has recognized that issues exist with presently known systems and methods for airway management and for assisting individuals to adequately support their head and neck in an upright position. The present disclosure provides a system and method for improved airway management and is configured to align the oropharyngeal, laryngeal and tracheal axes of a person's head and/or support a neck region and chin and posterior mandibular region of a person.

In one aspect, the present disclosure may provide an airway management device comprising a front end and a rear end defining a longitudinal direction therebetween, a first side and a second side defining a transverse direction therebetween, and a top and a bottom defining a vertical direction therebetween, a first base portion, and a second base portion; and wherein the first base portion and the second base portion are adapted to maintain a patent airway of a person.

In another aspect, the present disclosure may provide systems and methods for airway management. The airway management devices may be configured to align the oropharyngeal, laryngeal and tracheal axes of a person's head and/or support a neck region and chin and posterior mandibular region of a person. The airway management devices may provide forces similar to forces provided by a conventional head tilt chin lift maneuver and a conventional jaw thrust maneuver.

In another aspect, the present disclosure may provide a method of keeping a patient's airway open comprising providing a base including a first base portion and a second base portion; placing the base on a surface; placing a person's head on the second base portion; pivoting the first base portion relative to the second base portion from a neutral position to a deployed position; applying pressure to a person's chin with the first base portion; and lifting the person's chin so that the patient's airway is unobstructed. The applying of pressure to the patient's chin and lifting the patient's chin is accomplished without a caregiver contacting the patient's head with their hands. When the first base portion is in the neutral position the first base portion and the second base portion are aligned in a same plane and when the first base portion is in the deployed position the first base portion is oriented at an angle relative to the second base portion. In one example, the angle is an obtuse angle.

The method further includes applying pressure to the patient's chest via a pressure block extending outwardly from the first base portion. In one example, and prior to applying pressure to the patient's chest the method further includes detaching the pressure block from an interior region of the second base portion and operably engaging the pressure block with the first base portion. The method further includes compressing the pressure block via a securing assembly.

In one example, the pivoting of the first base portion to the deployed position further includes positioning a first base arm of the first base portion on a first side of the patient's head and positioning a second base arm of the first base portion on the other side of the patient's head. The method of claim 1, further includes positioning a back region of the patient's head within an aperture defined in the second base portion. The method of claim 1, further includes moving a region of the first base portion over a top and a front of the patient's head when moving the first base portion from the neutral position to the deployed position.

In another aspect, the present disclosure may provide an apparatus for aiding in keeping a patient's airway open, said apparatus comprising a base including a first base portion and a second base portion; wherein the first base portion is movable relative to the second base portion between a neutral position and a deployed position; and when the first base portion is in the deployed position the first base portion is configured to lift the patient's chin so that the patient's airway is unobstructed. In one example, when the first base portion is in the neutral position the first base portion and the second base portion are aligned in a same plane and when the first base portion is in the deployed position the first base portion is oriented at an angle relative to the second base portion. In one example, the angle is an obtuse angle.

The apparatus further includes a pressure block extending outwardly from the first base portion. When the first base portion is in the neutral position the pressure block is oriented perpendicular to the plane. The pressure block is selectively removable from the second base portion, and when the pressure block is removed from the second base portion, an aperture is defined in the second base portion.

The apparatus further includes a securing assembly operably engaged with the first base portion and configured to selectively compress the pressure block. In one example, the apparatus of claim 17 method of claim 11, wherein the securing assembly is a strap that is removably engaged with the first base portion.

In one example, the first base portion is substantially U-shaped in configuration and is integrally connected to the second base portion via a living hinge. The second base portion nests inside an opening defined in the substantially U-shaped first base portion when the first base portion is in the neutral position.

BRIEF DESCRIPTION OF THE SEVERAL VIEWS OF THE DRAWINGS

Sample embodiments of the present disclosure are set forth in the following description, is shown in the drawings and is particularly and distinctly pointed out and set forth in the appended claims.

Similar numbers refer to similar parts throughout the drawings.

DETAILED DESCRIPTION

Referring to FIG. 1-FIG. 5D, there is shown a first embodiment of an airway management device in accordance with one aspect of the present disclosure, with the airway management device generally indicated at 10. The airway management device 10 is adapted to be used by a person to align the oropharyngeal, laryngeal and tracheal axes of a person's head. The airway management device 10 may be configured to contact and provide various forces against person's base as further described below. As such, the airway management device 10 is made out of polyurethane foam to conform to the person's body and provide comfortability while providing suitable forces against the person's body. In one example, the airway management device 10 is made out of polyurethane foam having a density of 1.8 pounds per cubic foot; however, the airway management device 10 may be made of polyurethane foam having any suitable density. It is to be further understood that the airway management device 10 may be made out of any suitable materials.

Figure 1:
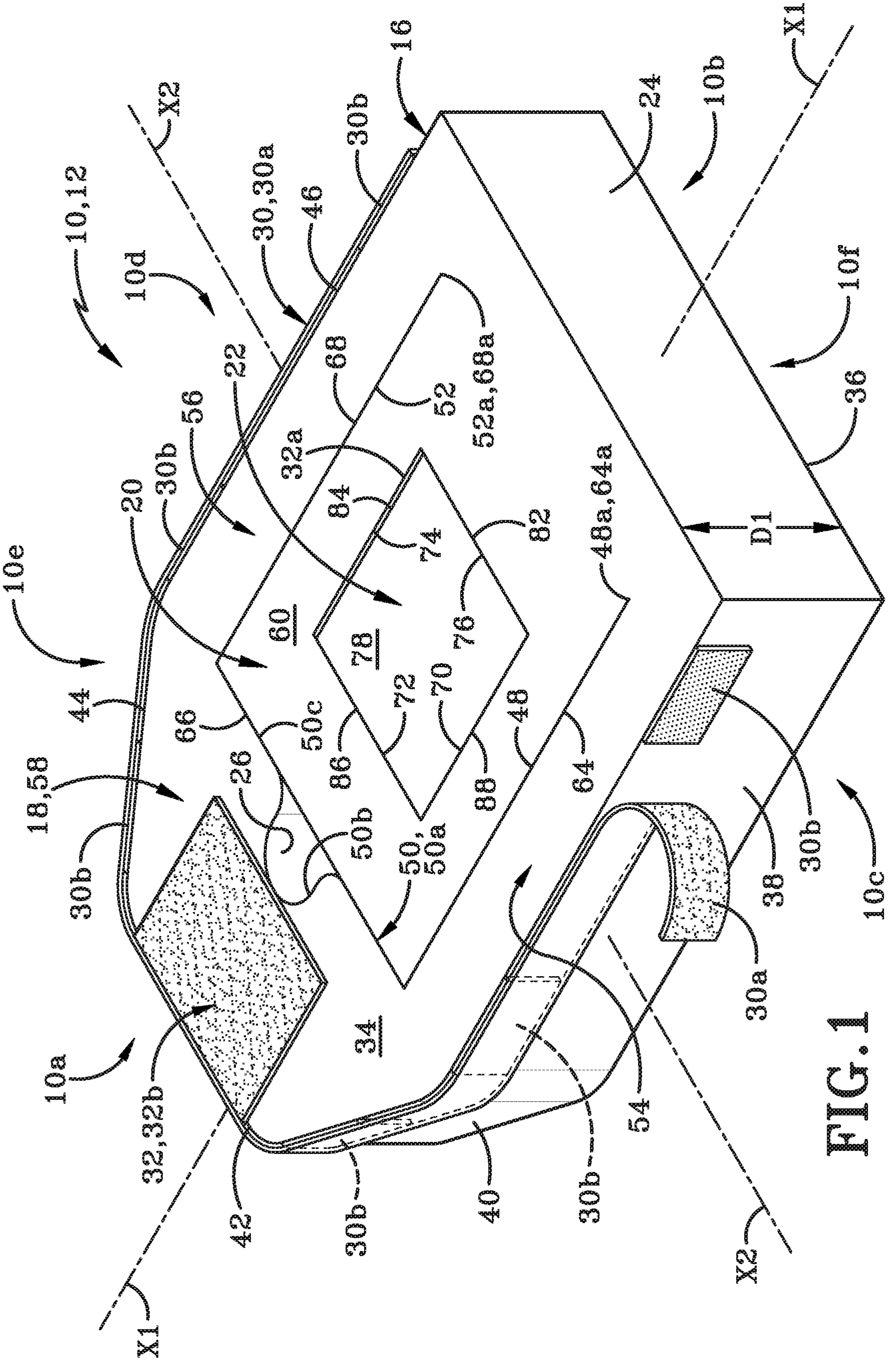
FIG. 1 is a rear top side perspective view of a first embodiment of an airway management device in accordance with one aspect of the present disclosure.
Figure 2:
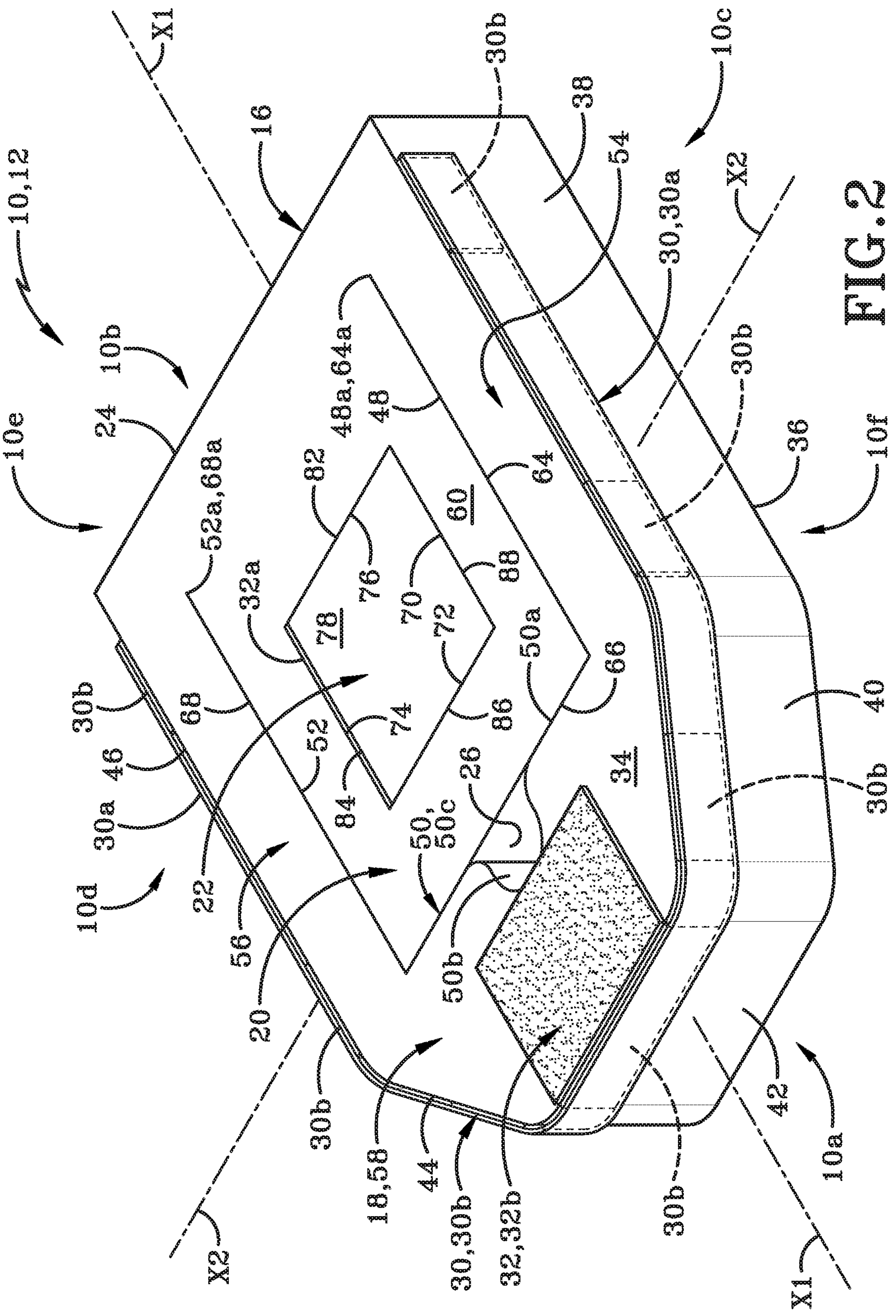
FIG. 2 is a front top side perspective view of the airway management device of FIG. 1.
Figure 3:
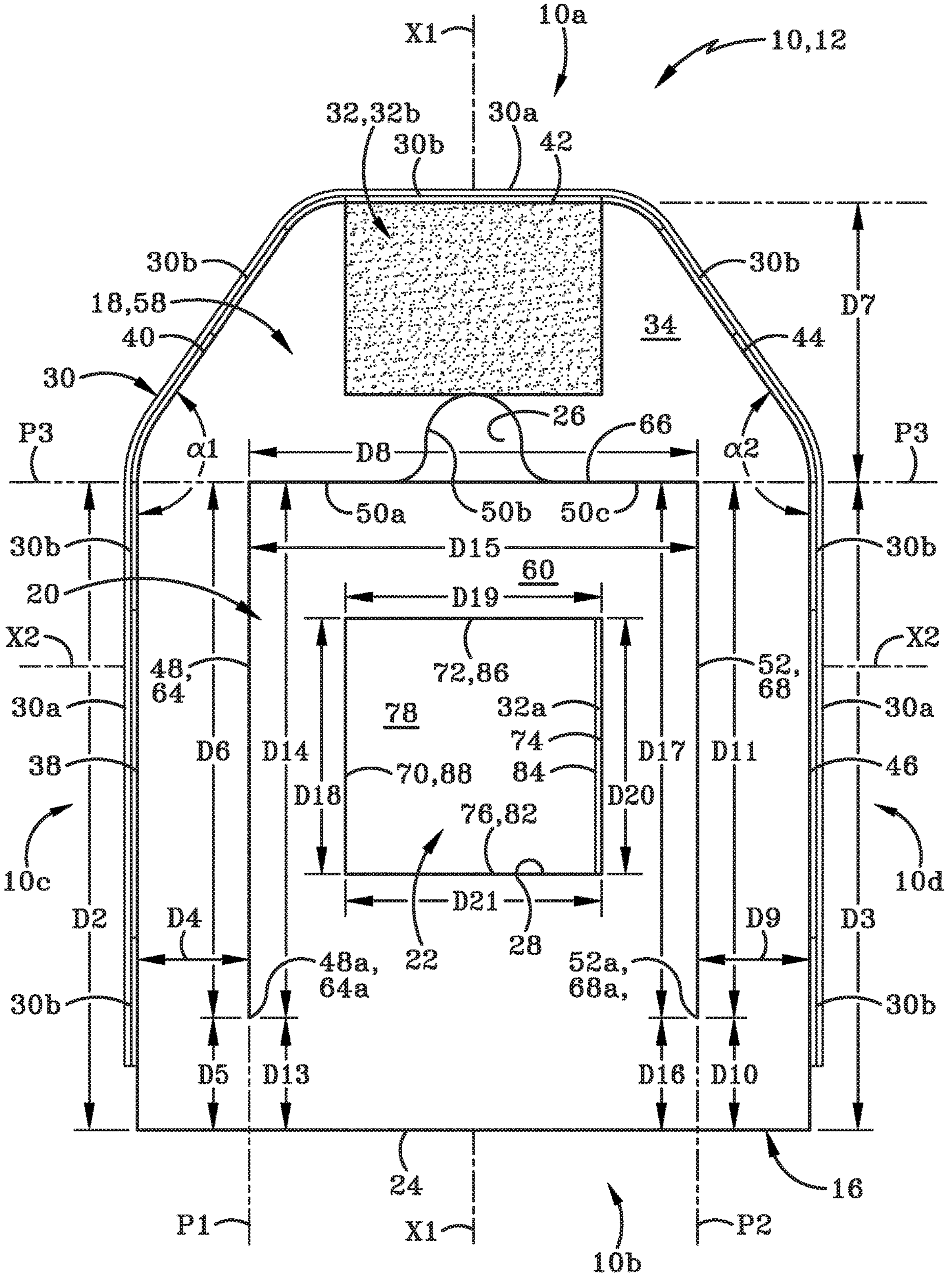
FIG. 3 is a top elevation view of the airway management device of FIG. 1.
Figure 4:
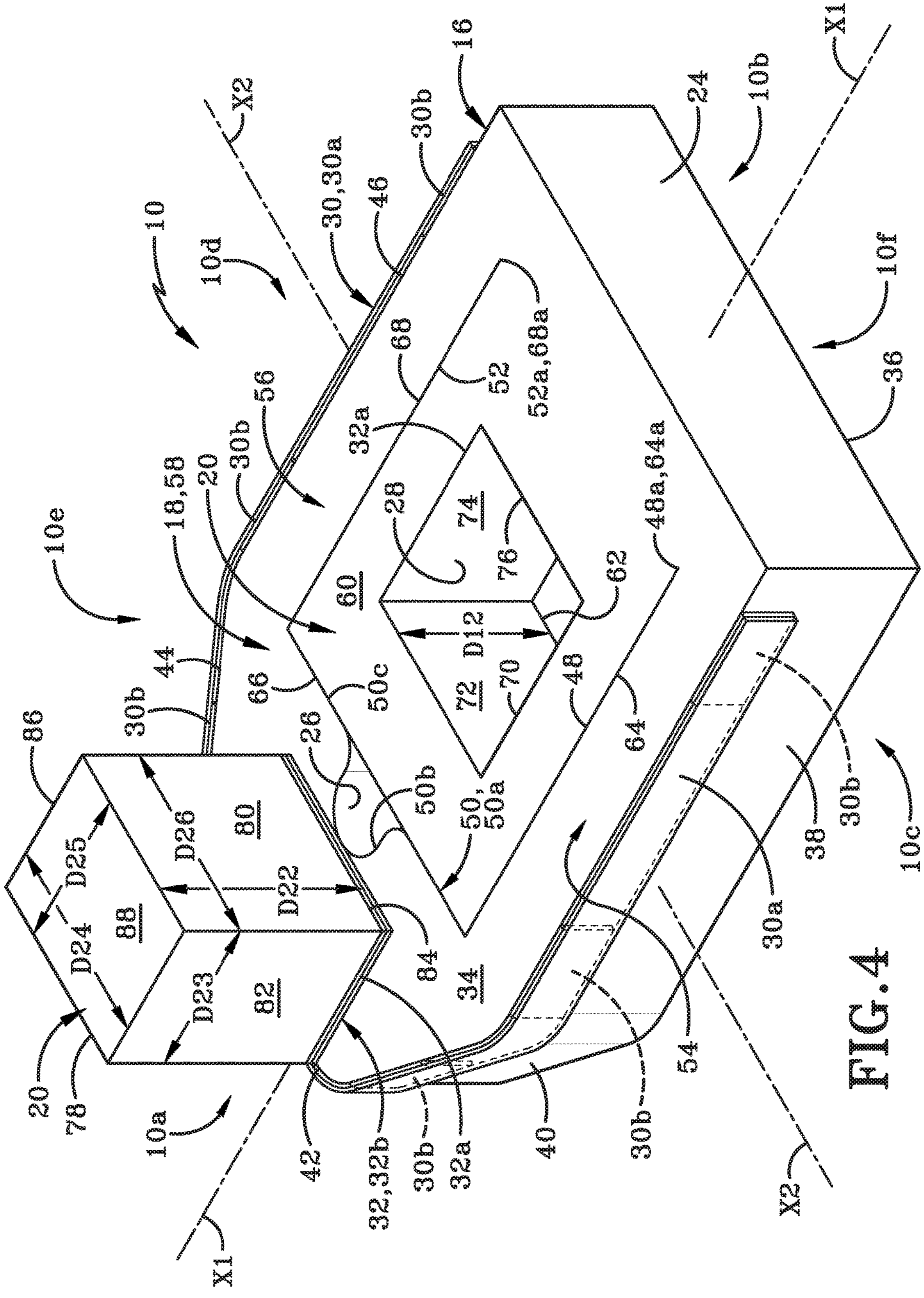
FIG. 4 is a rear top side perspective view of an airway management device with a third engaging member operably engaged with a first base portion.
Figure 5A:
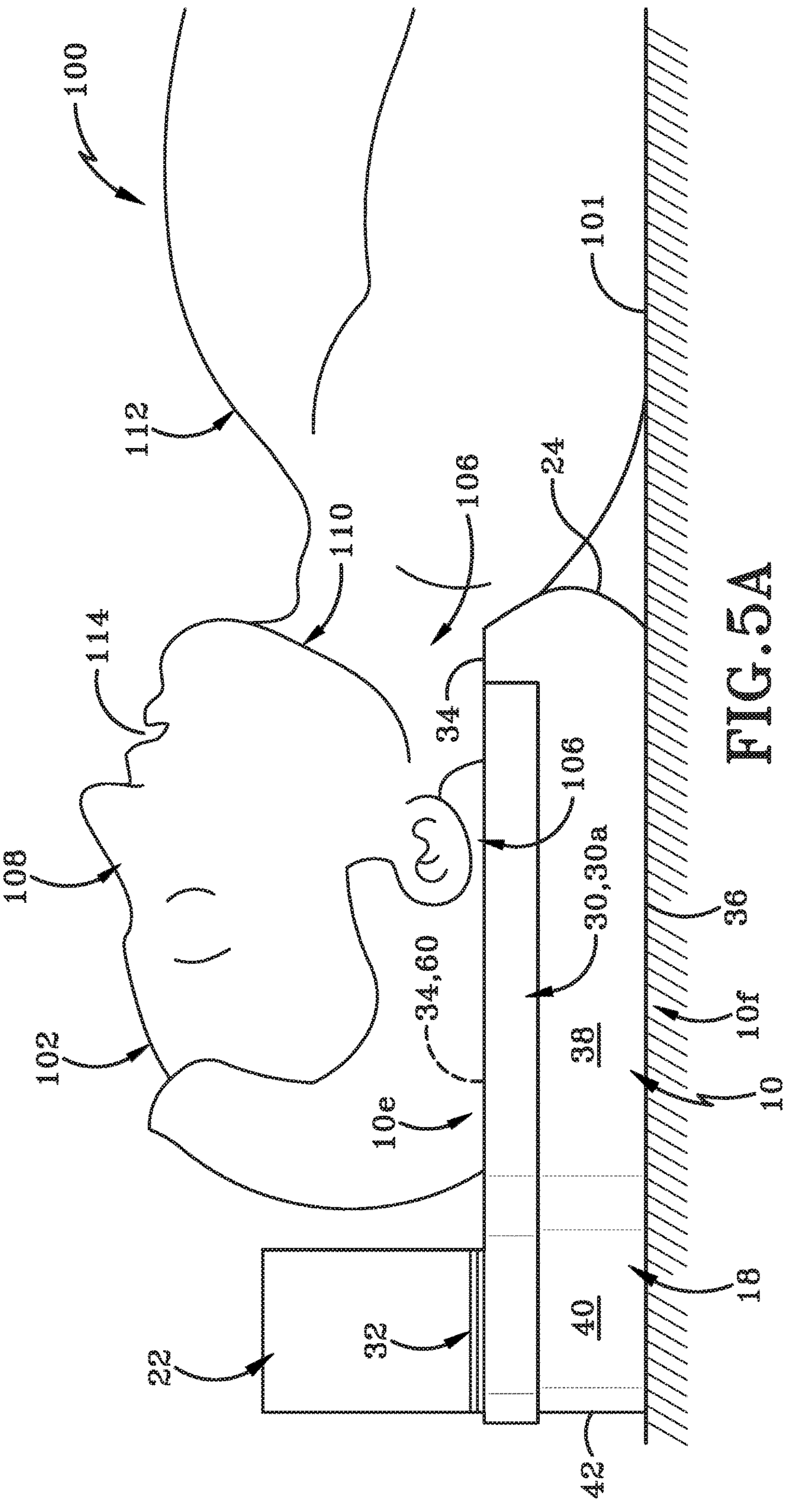
FIG. 5A is a side elevation view of the airway management device of FIG. 1 with a person operably engaged with a second base portion.
Figure 5B:
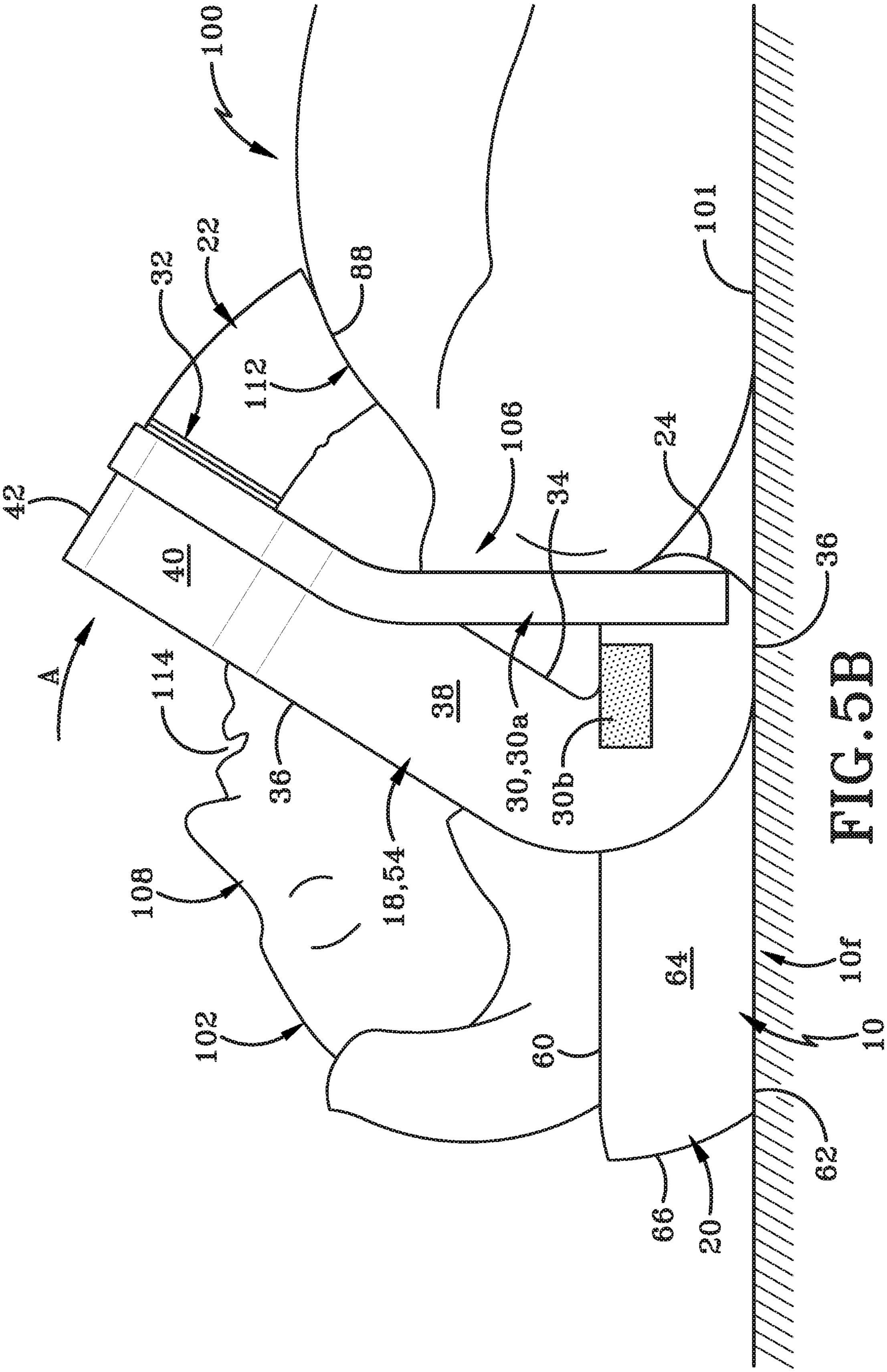
FIG. 5B is and operational view showing the airway management device of FIG. 1 being moved between a non-deployed position and a deployed position.
Figure 5C:
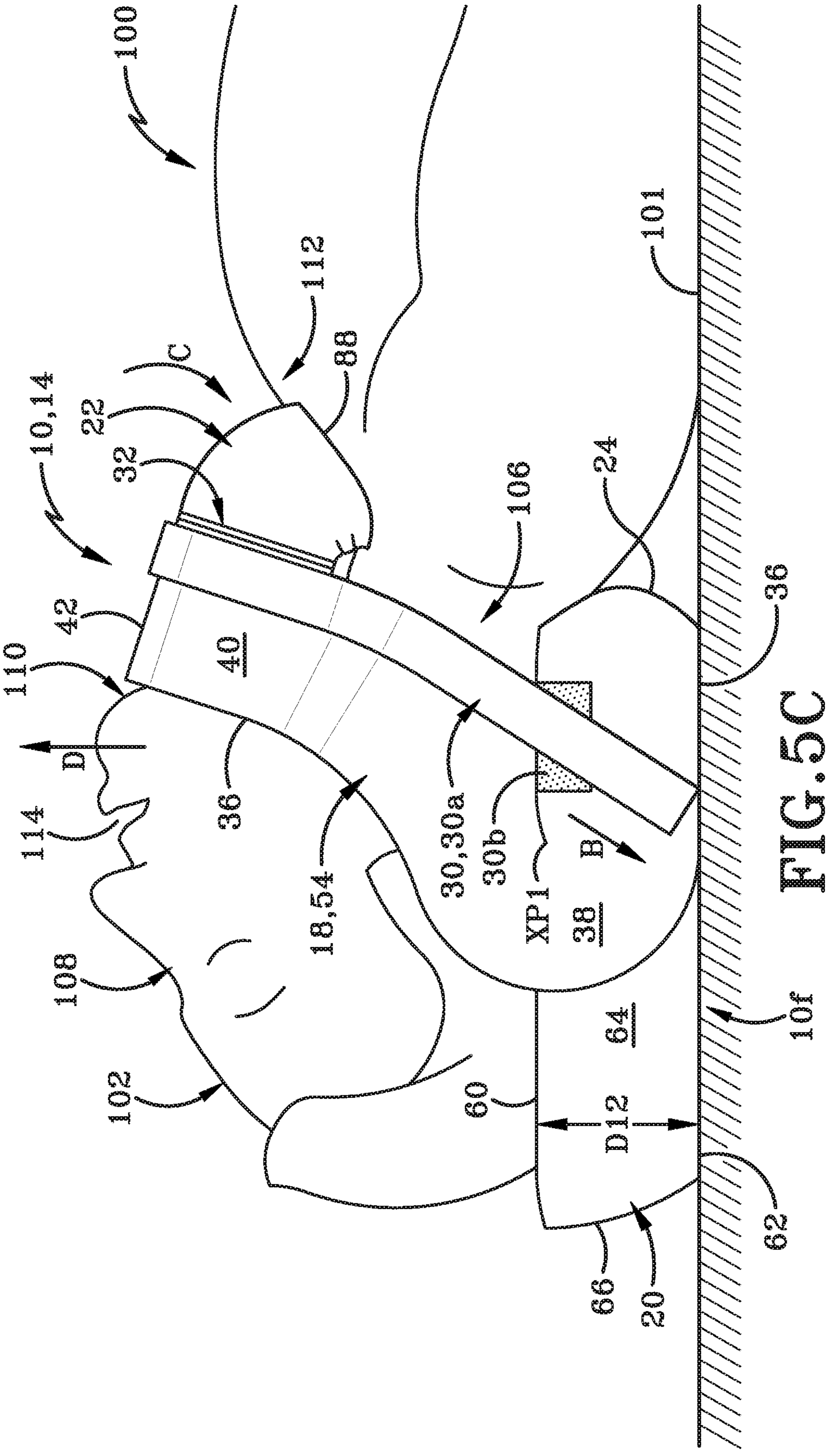
FIG. 5C is an operational view of the airway management device of FIG. 1 showing the first base portion contacting the chin and posterior mandibular region of the person, the second base portion contacting the occipital region of the person, and the third engaging member contacting a chest region of the person.
Figure 5D:
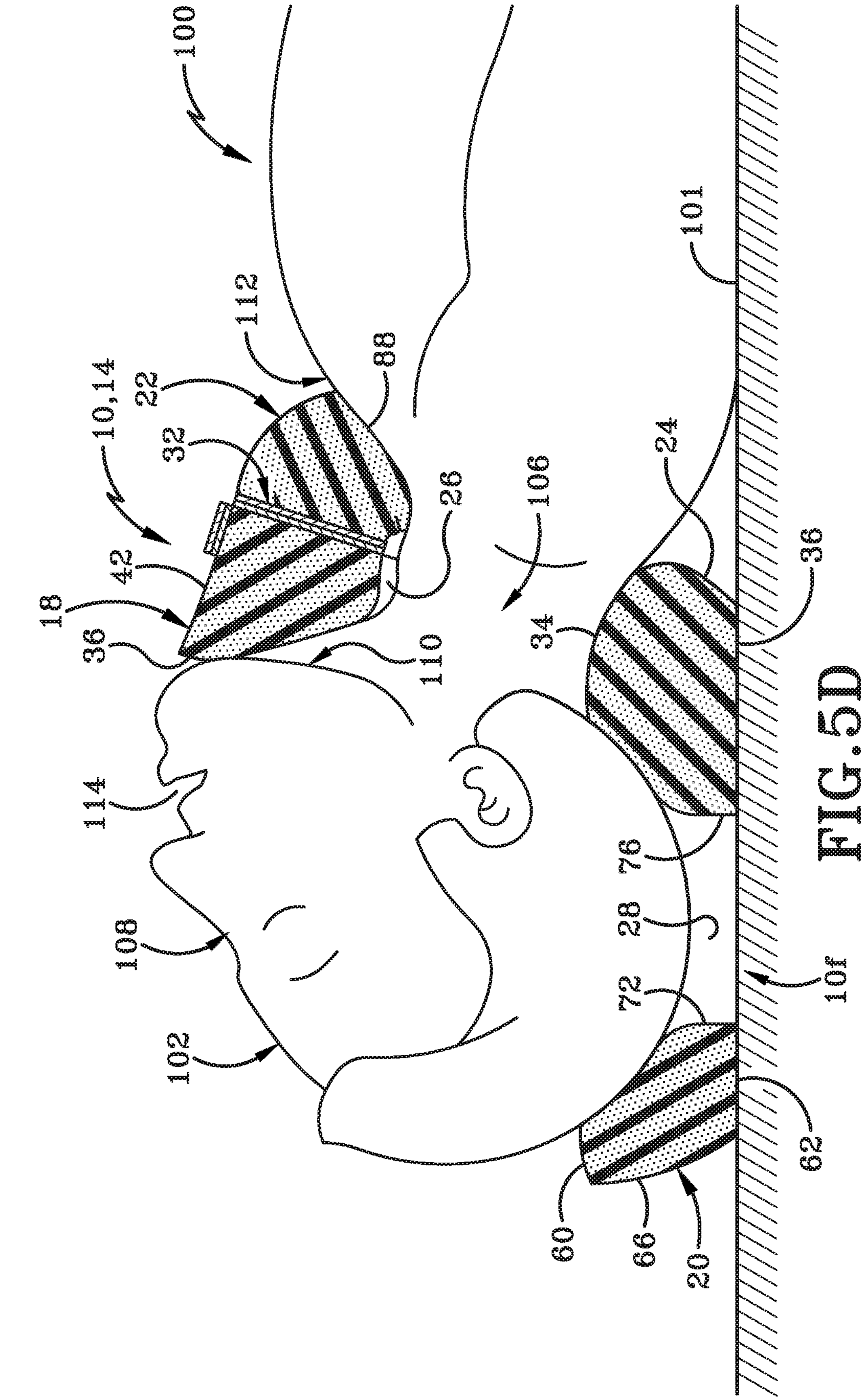
FIG. 5D is cross section view of FIG. 5C.

With reference to FIG. 1 through FIG. 5D, the airway management device 10 is configurable between a neutral, stored, or non-deployed position 12 (FIG. 1) and a deployed position 14 (FIG. 5C). When the airway management device 10 is viewed in the neutral position 12, the airway management device 10 includes a front end 10*a*, a rear end 10*b*, a first side 10*c*, a second side 10*d*, and a top 10*e* and a bottom 10*f*. The front end 10*a* and the rear end 10*b* define a longitudinal direction therebetween. The first side 10*c* and the second side 10*d* define a transverse direction therebetween. The top 10*e* and the bottom 10*f* define a vertical direction therebetween.

The airway management device 10 includes a longitudinal central axis X1 extending from the front end 10*a* to the rear end 10*b* and a transverse central axis X2 extending from the first side 10*c* to the second side 10*d*. The disclosure may make reference to certain components, walls, sides, surfaces, points and the like as being outer or inner which may respectively mean facing generally toward or away from the longitudinal central axis X1 or the transverse central axis X2. Components, walls, sides, surfaces, points and the like referenced as outer generally face away from the longitudinal central axis X1 or the transverse central axis X2 and components, walls, sides, surfaces, points and the like referenced as inner generally face toward the longitudinal central axis X1 or the transverse central axis X2.

In one embodiment, the airway management device 10 includes a base 16 having a first base portion 18, a second base portion 20, a pressure block 22, a rear wall 24, a notched portion 26 defined by the first base portion 18, and an aperture 28 defined by the second base portion 20. The airway management device 10 further includes a securing assembly 30, and a fastening assembly 32.

The first base portion 18 includes a top wall 34, a bottom wall 36, a first outer wall 38, a second outer wall 40, a third outer wall 42, a fourth outer wall 44, a fifth outer wall 46, a first inner wall 48, a second inner wall 50, a third inner wall 52, and a pivot axis XP1. The top wall 34 is be spaced a distance D1 from the bottom wall 36. In one example, the distance D1 may be approximately 3 inches; however, the distance D1 may be any suitable distance.

The first outer wall 38 is positioned between the top wall 34, the bottom wall 36, the rear wall 24, and the second outer wall 40. The second outer wall 40 is positioned between the top wall 34, the bottom wall 36, the third outer wall 42, and the first outer wall 38. The third outer wall 42 is positioned between the top wall 34, the bottom wall 36, the fourth outer wall 44 and the second outer wall 40. The fourth outer wall 44 is positioned between the top wall 34, the bottom wall 36, the fifth outer wall 46, and the third outer wall 42. The fifth outer wall 46 is positioned between the top wall 34, the bottom wall 36, the rear wall 24, and the fourth outer wall 44.

The first outer wall 38 extends generally longitudinally from the rear wall 24 to the second outer wall 40 a distance D2. In one example, the distance D2 may be approximately 10.125 inches; however, the distance D2 may be any suitable distance. The second outer wall 40 extends generally at an angle α1 from the first outer wall 38 to the third outer wall 42. In one example, the angle α1 is approximately 145 degrees relative to the first outer wall 38; however, the angle α1 may be any suitable angle. The third outer wall 42 extends generally transversely from the second outer wall 40 to the fourth outer wall 44. The fourth outer wall 44 extends generally at an angle α2 from the third outer wall 42 to the fifth outer wall 46. In one example, the angle α2 is approximately 145 degrees relative to the fifth outer wall 46; however, the angle α2 may be any suitable angle. The fifth outer wall 46 extends generally longitudinally from the fourth outer wall 44 to the rear wall 24 a distance D3. In one example, the distance D3 is approximately 10.125 inches; however, the distance D3 may be any suitable distance. The first outer wall 38 is generally parallel with the fifth outer wall 46 and the third outer wall 42 is generally parallel with the rear wall 24.

The first inner wall 48 is generally parallel to the first outer wall 38 and is spaced a distance D4 from the first outer wall 38. In one example, the distance D4 is approximately 1.75 inches; however, the distance D4 may be any suitable distance. The first inner wall 48 is positioned between the rear wall 24 and the second inner wall 50. The first inner wall 48 includes a rear end 48*a* spaced a distance D5 from the rear wall 24. In one example, the distance D5 is approximately 1.875 inches; however, the distance D5 may be any suitable distance. The first inner wall 48 extends longitudinally from the rear end 48*a* to the second inner wall 50 a distance D6. In one example, the distance D6 is approximately 8.25 inches; however, the distance D6 may be any suitable distance.

The second inner wall 50 is positioned between the first inner wall 48 and the third inner wall 52. The second inner wall 50 includes a first portion 50*a*, a second portion 50*b*, and a third portion 50*c*. The first portion 50*a* extends generally transversely from the first inner wall 48 to the second portion 50*b*. The second portion 50*b* extends generally in an arcuate manner between the first portion 50*a* and the third portion 50*c* to define the notched portion 26. The notched portion 26 is adapted to prevent tracheal compression and subsequent obstruction of the airway as well as provide comfortability to the person as further described below. The third portion 50*c* extends generally transversely from the second portion 50*b* to the third inner wall 52. The first portion 50*a* and the third portion 50*c* are generally parallel to the third outer wall 42 and are spaced a distance D7 from the third outer wall 42. In one example, the distance D7 is approximately 4.375 inches; however, the distance D7 may be any suitable distance. The second inner wall 50 extends generally transversely a distance D8 from the first inner wall 48 to the third inner wall 52. In one example, the distance D8 is approximately 7 inches; however, the distance D8 may be any suitable distance.

The third inner wall 52 is generally parallel to the fifth outer wall 46 and may be spaced a distance D9 from the fifth outer wall 46. In one example, the distance D9 is approximately 1.75 inches; however, the distance D9 may be any suitable distance. The third inner wall 52 is positioned between the rear wall 24 and the second inner wall 50. The third inner wall 52 includes a rear end 52*a* spaced a distance D10 from the rear wall 24. In one example, the distance D10 is approximately 1.875 inches; however, the distance D10 may be any suitable distance. The third inner wall 52 extends generally longitudinally from the rear edge 52*a* to the second inner wall 50 a distance D11. In one example, the distance D11 is approximately 8.25 inches; however, the distance D11 may be any suitable distance.

When the airway management device 10 is in the neutral position 12, the first base portion 18 further includes an imaginary vertical longitudinally extending first plane P1 defined by the first inner wall 48, an imaginary vertical transversely extending second plane P2 defined by the third inner wall 52, and an imaginary vertical longitudinally extending third plane P3 defined by the first portion 50*a* and the third portion 50*c* of the second inner wall 50. The first base portion 18 includes a first arm portion 54, a second arm portion 56 and an engaging portion 58.

When the airway management device 10 is in the neutral position 12, the first arm portion 54 is formed by and bounded by the top wall 34, the bottom wall 36, the first outer wall 38, the first inner wall 48, the rear wall 24, at least portion of the first plane P1, and at least a portion of the third plane P3.

When the airway management device 10 is in the neutral position 12, the second arm portion 56 is formed by and bounded by the top wall 34, the bottom wall 36, the fifth outer wall 46, the third inner wall 52, the rear wall 24, at least a portion of the second plane P2, and at least a portion of the third plane P3.

When the airway management device 10 is in the neutral position 12, the engaging portion 58 is formed by and bounded by the top wall 34, the bottom wall 36, the second outer wall 40, the third outer wall 42, the fourth outer wall 44, the second inner wall 50, and at least a portion of the second plane P2. In one example, the engaging portion is generally trapezoidal in shape; however, the engaging portion 58 may be any suitable shape.

The rear end 48*a* of the first inner wall 48 and the rear end 52*a* of the third inner wall 52 define the pivot axis XP1. In one example, the pivot axis XP1 is a living hinge; however, it is to be understood that the pivot axis XP1 may be any suitable pivot axis. The first base portion 18 is substantially U-shaped in configuration and is integrally connected to the second base portion 20 via the living hinge. The second base portion 20 nests inside an opening 53 defined in the substantially U-shaped first base portion 18 when the first base portion 18 is in the neutral position. The airway management device 10 is configurable between the neutral position 12 and the deployed position 14 by pivoting the first base portion 18 about the pivot axis XP1. Specifically, the first arm portion 54, the second arm portion 56, and the engaging portion 58 are pivoted about the pivot axis XP1 as more fully described below.

The second base portion 20 includes a top wall 60, a bottom wall 62, a first outer wall 64, a second outer wall 66, a third outer wall 68, first inner wall 70, a second inner wall 72, a third inner wall 74, and a fourth inner wall 76. The top wall 60 is spaced a distance D12 from the bottom wall 62. In one example, the distance D12 is approximately 3 inches; however, the distance D12 may be any suitable distance.

The first outer wall 64 is positioned between the top wall 60, the bottom wall 62, the rear wall 24 and the second outer wall 66. The second outer wall 66 is positioned between the top wall 60, the bottom wall 62, first outer wall 64, and the third outer wall 68. The third outer wall 68 is positioned between the top wall 60, the bottom wall 62, the rear wall 24 and the second outer wall 66.

The first outer wall 64 includes a rear end 64*a* spaced a distance D13 from the rear wall 24. In one example, the distance D13 is approximately 1.875 inches; however, the distance D13 may be any suitable distance. The first outer wall 64 extends longitudinally from the rear end 64*a* to the second outer wall 66 a distance D14. In one example, the distance D14 is approximately 8.25 inches; however, the distance D14 may be any suitable distance. When the airway management device 10 is in the neutral position 12, the first inner wall 48 of the first base portion 18 is proximate and generally parallel to the first outer wall 64 of the second base portion 20. As such, and in one example, the distance D6 is equal to the distance D14; however, in other examples, the distance D6 and the distance D14 may be different distances.

The second outer wall 66 extends generally transversely a distance D15 from the first outer wall 64 to the third outer wall 68. In one example, the distance D15 is approximately 7 inches; however, the distance D15 may be any suitable distance. When the airway management device 10 is in the neutral position 12, the second inner wall 50 of the first base portion 18 is proximate and generally parallel to the second outer wall 66 of the second base portion 20. As such, and in one example, the distance D8 is equal to the distance D15; however, in other examples, the distance D8 and the distance D15 may be different distances.

The third outer wall 68 includes a rear end 68*a* spaced a distance D16 from the rear wall 24. In one example, the distance D16 is approximately 1.875 inches; however, the distance D16 may be any suitable distance. The third outer wall 68 extends generally longitudinally from the rear end 68*a* to the second outer wall 66 a distance D17. In one example, the distance D17 is approximately 8.25 inches; however, the distance D17 may be any suitable distance. When the airway management device 10 is in the neutral position 12, the third inner wall 52 of the first base portion 18 is proximate and generally parallel to the third outer wall 68 of the second base portion 20. As such, and in one example, the distance D11 is equal to the distance D17; however, in other examples, the distance D11 and the distance D17 may be different distances.

When the airway management device 10 is in the neutral position 12, the first outer wall 64 is generally longitudinally aligned with the first plane P1 and the third outer wall 68 is longitudinally aligned with the second plane P2. The top wall 60 is bounded by the first outer wall 60, the second outer wall 62, the third outer wall 64, the first inner wall 70, the second inner wall 72, the third inner wall 74, the fourth inner wall 76, the first plane P1 and the second plane P2.

The first inner wall 70 is positioned between the top wall 60, the bottom wall 62, the second inner wall 72 and the fourth inner wall 76. The second inner wall 72 is positioned between the top wall 60, the bottom wall 62, the first inner wall 70 and the third inner wall 74. The third inner wall 74 is positioned between the top wall 60, the bottom wall 62, the second inner wall 72 and the fourth inner wall 76. The fourth inner wall 76 is positioned between the top wall 60, the bottom wall 62, the first inner wall 70 and the third inner wall 74. As such, the first inner wall 70 is generally parallel to and generally faces the third inner wall 74, and the second inner wall 72 is generally parallel to and generally faces the fourth inner wall 76.

The first inner wall 70 extends generally longitudinally from the fourth inner wall 76 to the second inner wall 72 a distance D18. In one example, the distance D18 may be approximately 4 inches; however, the distance D18 may be any suitable distance. The second inner wall 72 extends generally transversely from the first inner wall 70 to the third inner wall 74 a distance D19. In one example, the distance D19 is approximately 4 inches; however, the distance D19 may be any suitable distance. The third inner wall 74 extends generally longitudinally from the second inner wall 72 to the fourth inner wall 76 a distance D20. In one example, the distance D20 is approximately 4 inches; however, the distance D20 may be any suitable distance. The fourth inner wall 76 extends generally transversely from the third inner wall 74 to the first inner wall 70 a distance D21. In one example, the distance D21 may be approximately 4 inches; however, the distance D21 may be any suitable distance. The first inner wall 70, the second inner wall 72, the third inner wall 74, and the fourth inner wall 76 define the aperture 28 which extends vertically through the base 16.

The pressure block 22 includes a top wall 78, a bottom wall 80, a first outer wall 82, a second outer wall 84, a third outer wall 86, and a fourth outer wall 88. In one example, the pressure block 22 is generally square or rectangular shaped; however, the pressure block 22 may be any suitable shape.

The top wall 78 is spaced a distance D22 from the bottom wall 80. In one example, the distance D22 is approximately 3 inches; however, the distance D22 may be any suitable distance. The first outer wall 82 is positioned between the top wall 78, the bottom wall 80, the second outer wall 84, and the fourth outer wall 88. The second outer wall 84 is positioned between the top wall 78, the bottom wall 80, the third outer wall 86 and the first outer wall 82. The third outer wall 86 is positioned between the top wall 78, the bottom wall 80, the fourth outer wall 88, and the second outer wall 84. The fourth outer wall 88 is positioned between the top wall 78, the bottom wall 80, the first outer wall 82 and the third outer wall 86.

The first outer wall 82 extends generally longitudinally from the fourth outer wall 88 to the second outer wall 84 a distance D23. In one example, the distance D23 is approximately 4 inches; however, the distance D23 may be any suitable distance. The second outer wall extends generally transversely from the first outer wall 82 to the third outer wall 86 a distance D24. In one example, the distance D24 is approximately 4 inches; however, the distance D24 may be any suitable distance.

The third outer wall 86 extends generally longitudinally from the fourth outer wall 88 to the second outer wall 84 a distance D25. In one example, the distance D25 is approximately 4 inches; however, the distance D25 may be any suitable distance. The fourth outer wall extends generally transversely from the third outer wall 86 to the first outer wall 82 a distance D26. In one example, the distance D26 is approximately 4 inches; however, the distance D26 may be any suitable distance.

The top wall 78 is generally parallel to and generally faces away from the bottom wall 80, the first outer wall 82 is generally parallel to and generally faces away from the third outer wall 86, and the second outer wall 84 is generally parallel to and generally faces away from the fourth outer wall 88.

When the airway management device 10 is in the neutral position 12, the pressure block 22 is operationally engaged with the base 16. In one example, the pressure block 22 is releasably held within the aperture 28 via an interference fit between the first outer wall 82, the second outer wall 84, the third outer wall 86, and the fourth outer wall 88 of the pressure block 22 and the first inner wall 70, the second inner wall 72, the third inner wall 74, and the fourth inner wall 76 of the second base portion 20.

The securing assembly 30 includes a securing member 30*a* and a plurality of securing points 30*b*. The securing member 30*a* is a strap with hooks and the plurality of securing points 30*b* are patches of material including loops; however, it is to be understood that the securing member 30*a* could alternatively be a strap with loops and the plurality of securing points 30*b* could be patches of material including hooks. In one example, the securing assembly 30 includes seven securing points 30*b* where one connection point 30*b* is provided on the first outer wall 38 of the first base portion 18 proximate the top wall 34 and the rear wall 24, one connection point 30*b* is provided on the first outer wall 38 proximate the top wall and the second outer wall 40, one connection point 30*b* is provided on the second outer wall 40 proximate the top wall 34 and the third outer wall 42, one connection point 30*b* is provided on the third outer wall 42 proximate the top wall 34 and the fourth outer wall 44, one connection point 30*b* is provided on the fourth outer wall 44 proximate the top wall 34 and the third outer wall 42, one connection point is provided on the fifth outer wall 46 proximate the top wall 34 and the fourth outer wall 44, and one connection point 30*b* is provided on the fifth outer wall 46 proximate the top wall 34 and the rear wall 24. When the airway management device 10 is viewed in the neutral position 12, the securing member 30*a* (i.e., the strap) is operably engaged with the securing points 30*b* such that the strap is operably engaged to the first outer wall 38, the second outer wall 40, the third outer wall 42, the fourth outer wall 44, and the fifth outer wall 46 proximate the top wall 34. The securing member 30*a* and the plurality of securing points 30*b* may be any suitable size.

Although particular positions of the securing points 30*b* have been described, it is to be understood that the securing points 30*b* may be provided in any suitable locations. Further, although the securing assembly 30 has been described as having a hook and loop engagement mechanism, it is to be understood that the securing assembly 30 may utilize any suitable securing mechanisms, including, but not limited to, adhesives or mechanical connections.

The fastening assembly 32 includes a fastening mechanism 32*a* and at least one fastening point 32*b*. The fastening mechanism 32*a* is a patch of material including hooks and the at least one connection 32*b* is a patch of material including loops; however, it is to be understood that the fastening mechanism 32*a* could alternatively be a patch of material with loops and the at least one fastening point 32*b* could be a patch of material including hooks. The fastening mechanism 32*a* (i.e., the patch of material including hooks) is provided on the first outer wall 82 of the pressure block 22 and the at least one fastening point 32*b* is provided on the top wall 34 of the engaging portion 58 proximate the third outer wall 42 and the first aperture 26. The pressure block 22 is operably engaged with the engaging portion 58 of the first base portion 18 by releasably securing the fastening mechanism 32*a* to the at least one connection 32*b* as further described below. The fastening mechanism 32*a* and the at least one fastening point 32*b* may be any suitable size.

Although a particular position of the fastening mechanism 32*a* and the at least one securing points 32*b* have been described, it is to be understood that the fastening mechanism 32*a* and the at least one fastening point 32*b* may be provided in any suitable location. Further, although the fastening assembly 32 has been described as having a hook and loop engagement mechanism, it is to be understood that the fastening assembly 32 may utilize any suitable fastening mechanisms, including, but not limited to, adhesives or mechanical fasteners.

With primary reference to FIG. 5A through FIG. 5D, and in operation, the airway management device 10 is utilized by a person 100 to restore and/or maintain a patent airway. The airway management device 10 is placed on a surface 101. The airway management device is configurable between a neutral position 12 (FIG. 5A) and a deployed position 14 (FIG. 5C and FIG. 5D) to support various portions of a head 102 of the person.

In operation, the pressure block 22 is removed from the aperture 28 and releasably secured to the first base portion 18. Specifically, and in one embodiment, the fastening mechanism 32*a* (i.e., the patch including hooks, which, in an alternative embodiment, may include loops instead of hooks which may be connected to hooks in a separate component) provided on the first outer wall 82 of the pressure block 22 is operably engaged with the fastening point 32*b* provided on the top wall 34 of the engaging portion 58 (FIG. 5A).

As shown in FIG. 5A, when the person 100 is in the supine position, the second base portion 20 supports an occipital region 104 of the head 102 of the person 100 and a neck region 106 of the person 100. At least a portion of the occipital region 104 of the head 102 of the person 100 is received within the aperture 28 and at least a portion of the occipital region 104 of the head 102 of the person 100 and the neck region 106 of the person 100 is supported by the top wall 60, the first inner wall, 70, the second inner wall 72, the third inner wall 74, and the fourth inner wall 76 between the first plane P1 and the second plane P2.

In operation, and as shown in FIG. 5C, the first base portion 18 is pivoted about the pivot axis XP1 over a face 108 of the person 100 in a direction generally indicated by arrow A. An operator (not shown) may grasp at least a portion of the second portion 50*b* of the second inner wall 50 to aid in pivoting the first base portion 18 about the pivot axis XP1. The notched portion 26 receives a trachea (not shown) of the person 100 so to prevent unsuitable compression against the trachea of the person 100. As shown in FIG. 5B, the bottom wall 36 of the first base portion 18 contacts a chin and posterior mandibular region 110 of the person 100 and the bottom wall 62 of the pressure block 22 contacts a chest region 112 of the person 100.

As shown in FIG. 5C, the securing assembly 30 provides a force in a direction indicated generally by arrow B. As shown in FIG. 5C, the force provided by the securing assembly 30 compresses the pressure block 22 in a direction generally indicated by arrow C. The pressure block 22 and the first base portion 18 provide a force to the chin and posterior mandibular region 110 of the person 100 in a general direction indicated by arrow D which aligns the axes of a mouth 114, pharynx (not shown) and larynx (not shown) of the person 100 into alignment. The alignment of the axes may also be referred to as a "sniffing position." The sniffing position opens up the airway of the person 100 by lifting a tongue (not shown) away from the back of a throat (not shown) of the person 100.

Although the airway management device 10 has been described as having various components operably engaged with one another in a particular manner, it is to be understood that some components may be integrally formed with the airway management device 10 while other components are separate from yet operably engaged with the airway management device 10. For example, and not meant as a limitation, instead of the first base portion 18, which includes the first arm portion 54, the second arm portion 56 and the engaging portion 58, being integrally formed with the airway management device 10, it is entirely possible that the first base portion 18 may be operably engaged by connecting the first base portion 18 to the second base portion 20 in any suitable manner. In another non-limiting example, instead of the pressure block 22 being operably engaged with the first base portion 38 via the fastening assembly 32, it is to be understood that the pressure block 22 may be integrally formed with the first base portion 18.

Referring to FIG. 6-FIG. 11E, there is shown a second embodiment of an airway management device in accordance with one aspect of the present disclosure, with the airway management device generally indicated at 1000. The airway management device 1000 is adapted to be used by a person to align the oropharyngeal, laryngeal and tracheal axes of a person's head as more fully described below. The airway management device 1000 is configured to contact and provide various forces against a person's body as further described below. As such, and in one example, the airway management device 1000 is made out of polyurethane foam to conform to the person's body and provide comfortability while providing suitable forces against the person's body. In one example, the airway management device 1000 is made out of polyurethane foam having a density of 1.8 pounds per cubic foot; however, the airway management device 1000 may be made of polyurethane foam having any suitable density. Although the airway management device 1000 has been described as being made out of polyurethane foam, it is to be entirely understood that the airway management device 1000 may be made out of any suitable materials.

Figure 11A:
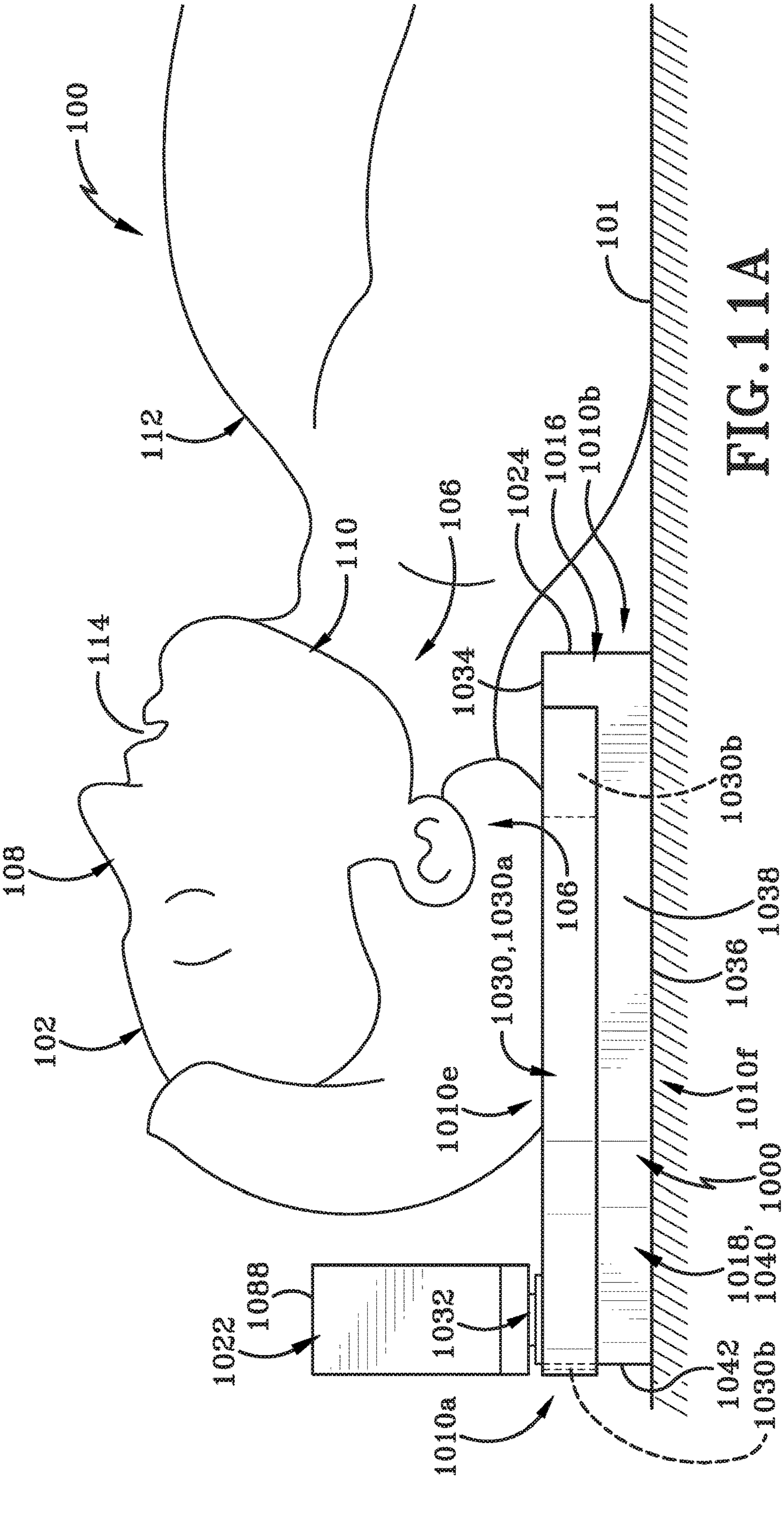
FIG. 11A is a side elevation view of the airway management device of FIG. 6 with a person operably engaged with a second base portion.
Figure 11B:
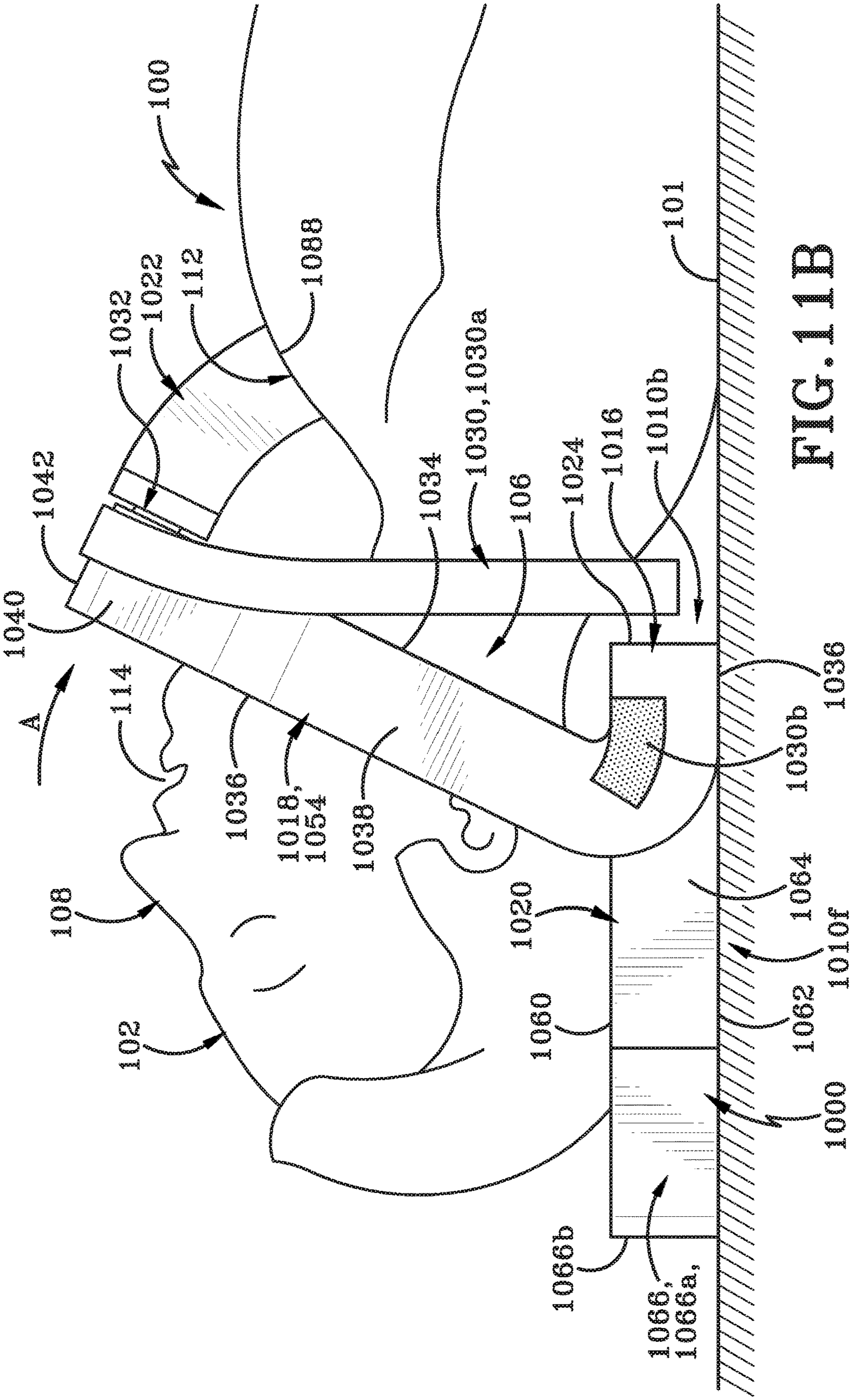
FIG. 11B is and operational view showing the airway management device of FIG. 6 being moved between a non-deployed position and a deployed position.
Figure 11C:
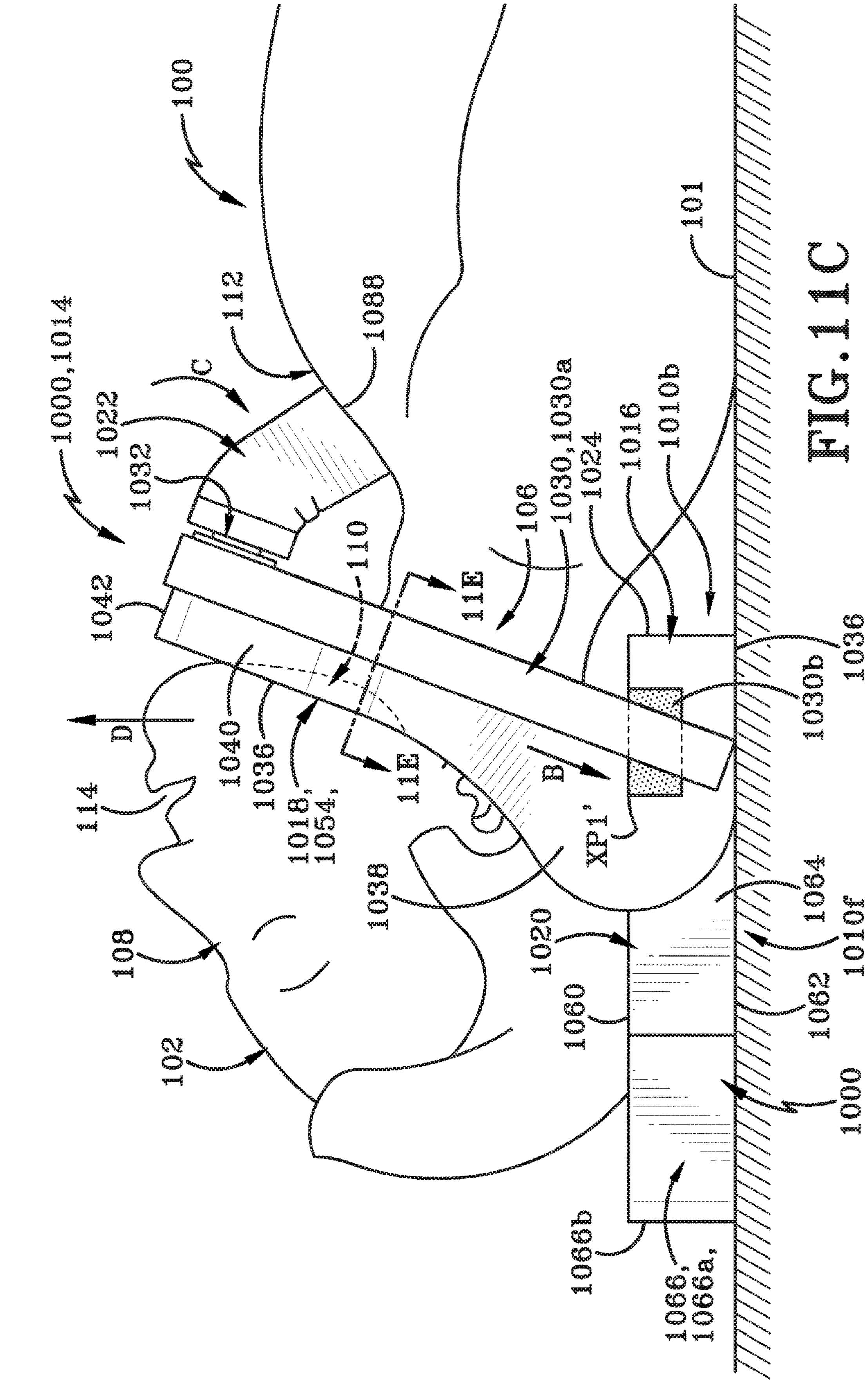
FIG. 11C is an operational view of the airway management device of FIG. 6 showing the first base portion contacting the chin and posterior mandibular region of the person, the second base portion contacting the occipital region of the person, and the third engaging member contacting a chest region of the person.
Figure 11D:
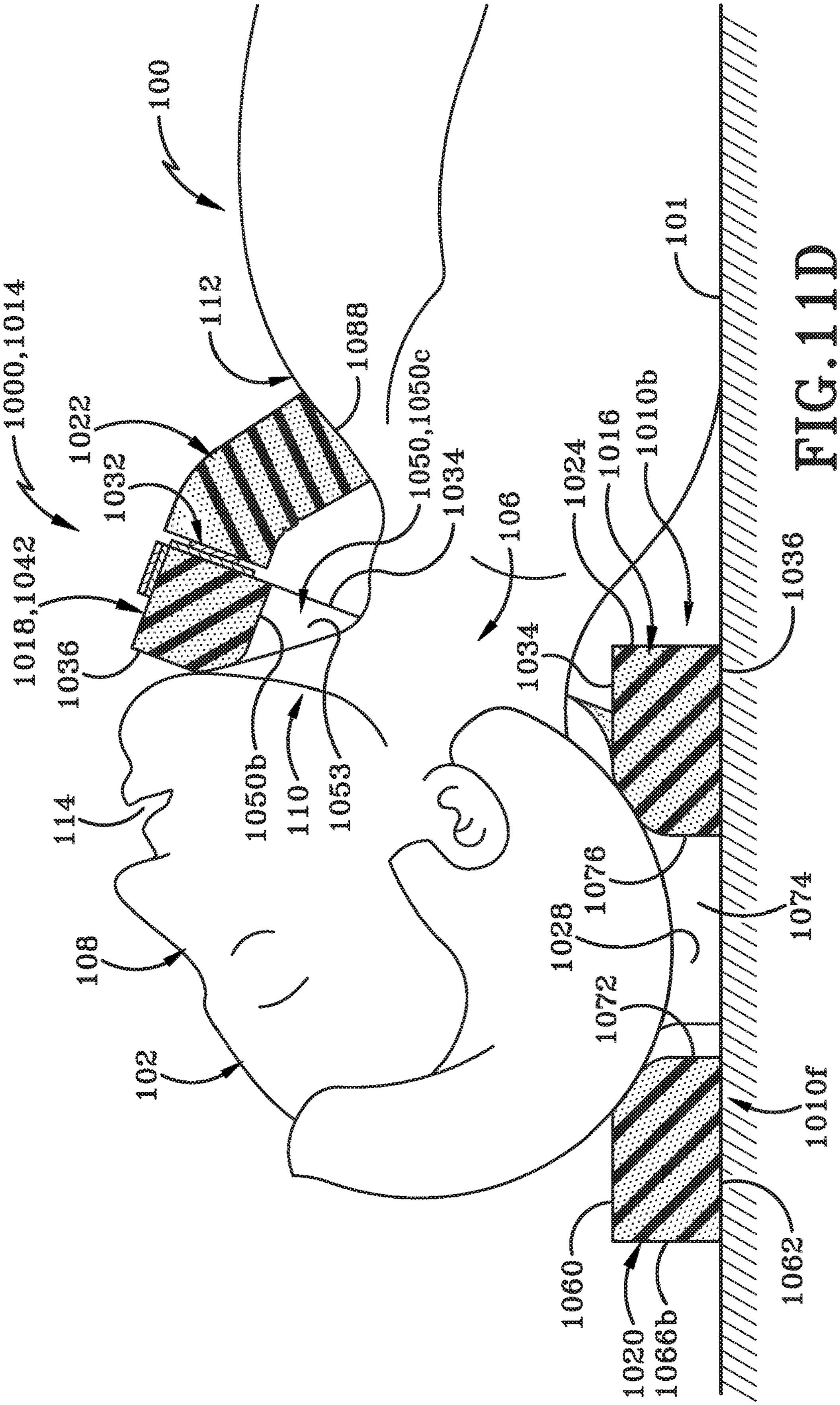
FIG. 11D is side cross section view of FIG. 11C.
Figure 11E:
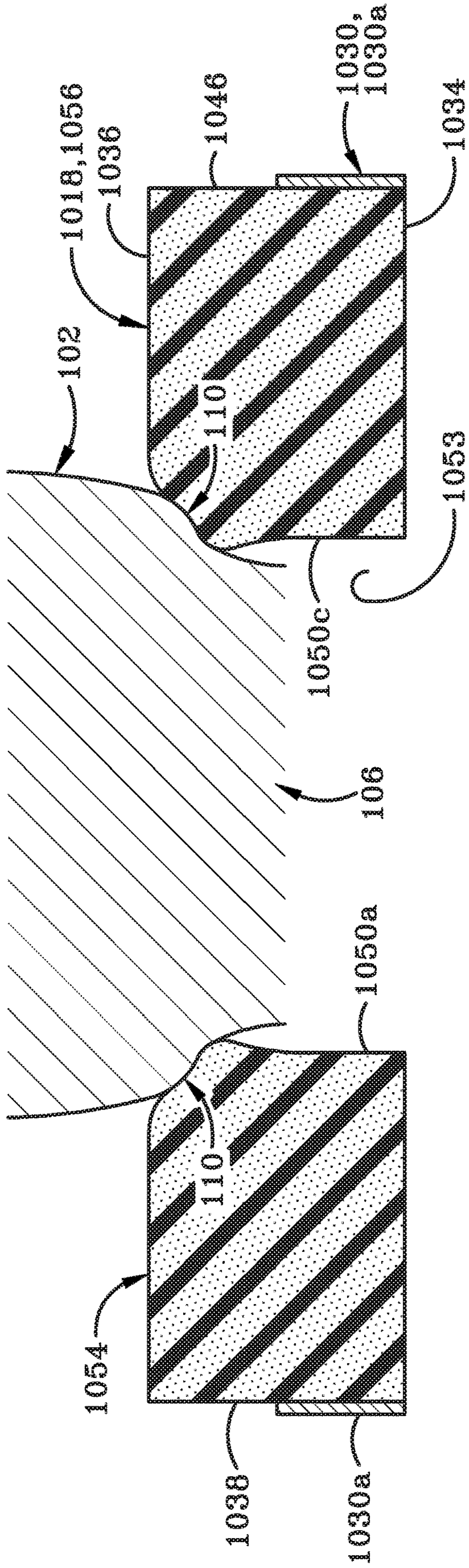
FIG. 11E is a rear cross section view of FIG. 11C.
Figure 12:
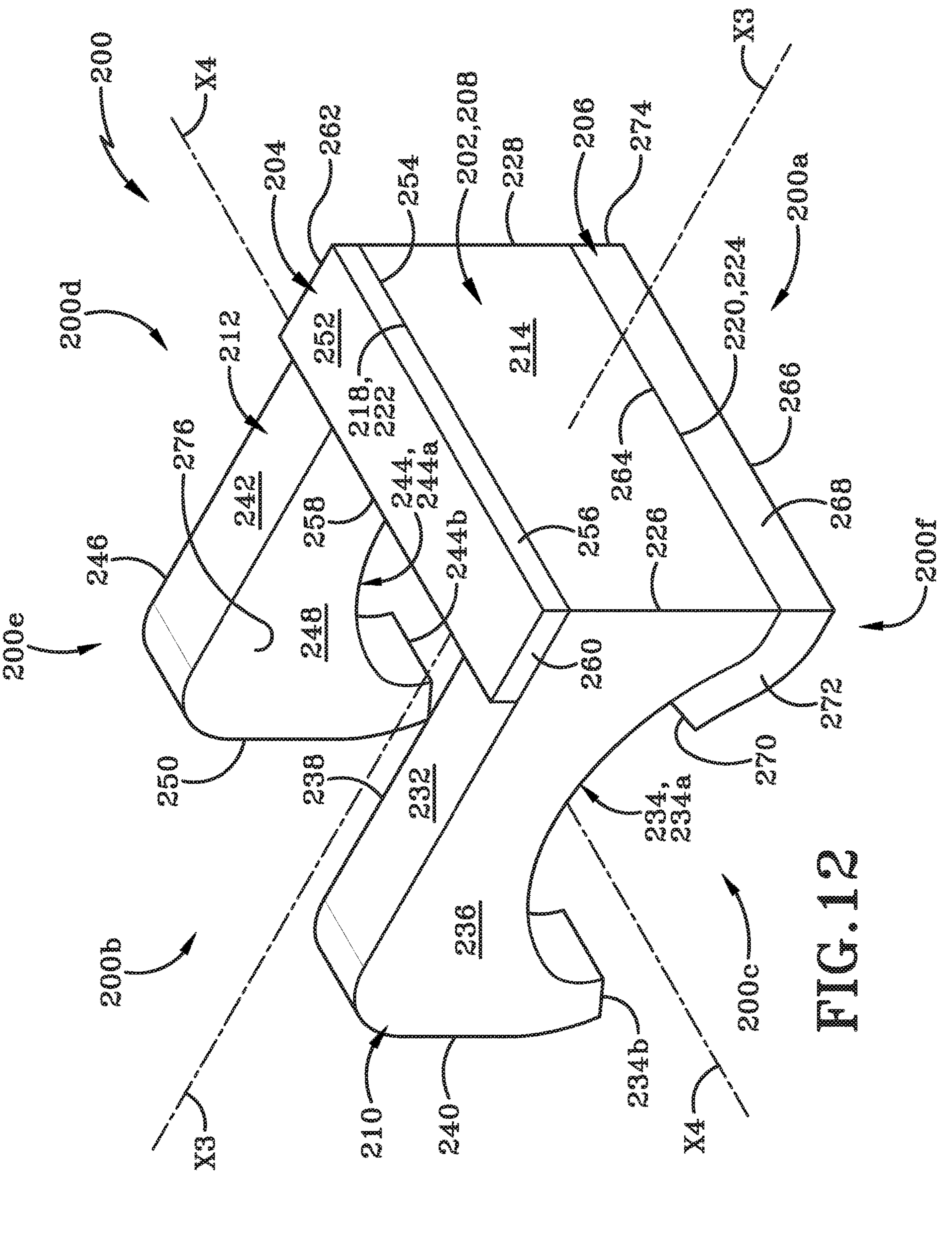
FIG. 12 is a front top side perspective view of a third embodiment of an airway management device in accordance with one aspect of the present disclosure.
Figure 13:
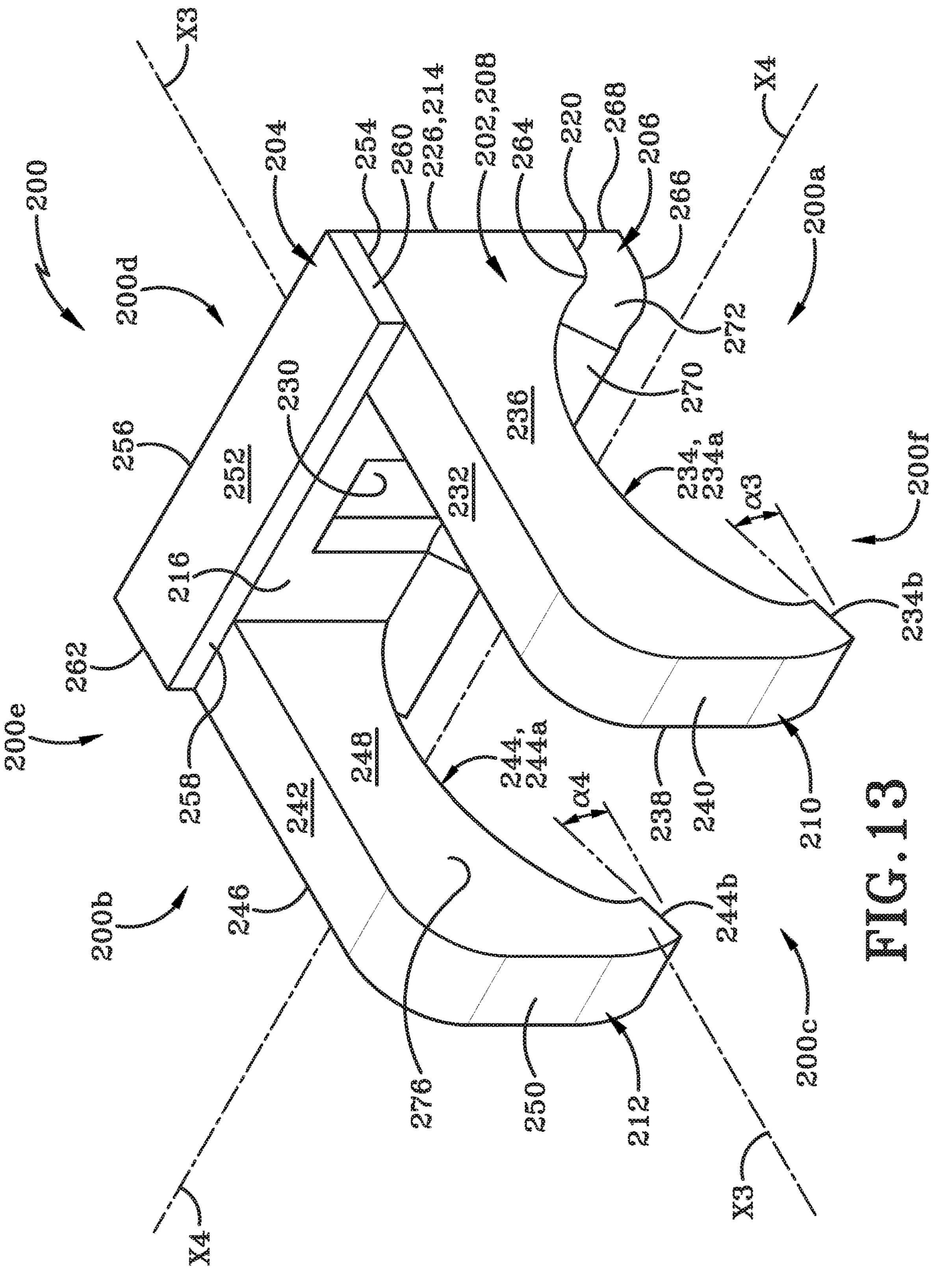
FIG. 13 is a rear top side perspective view of one embodiment of the airway management device of FIG. 12.
Figure 14:
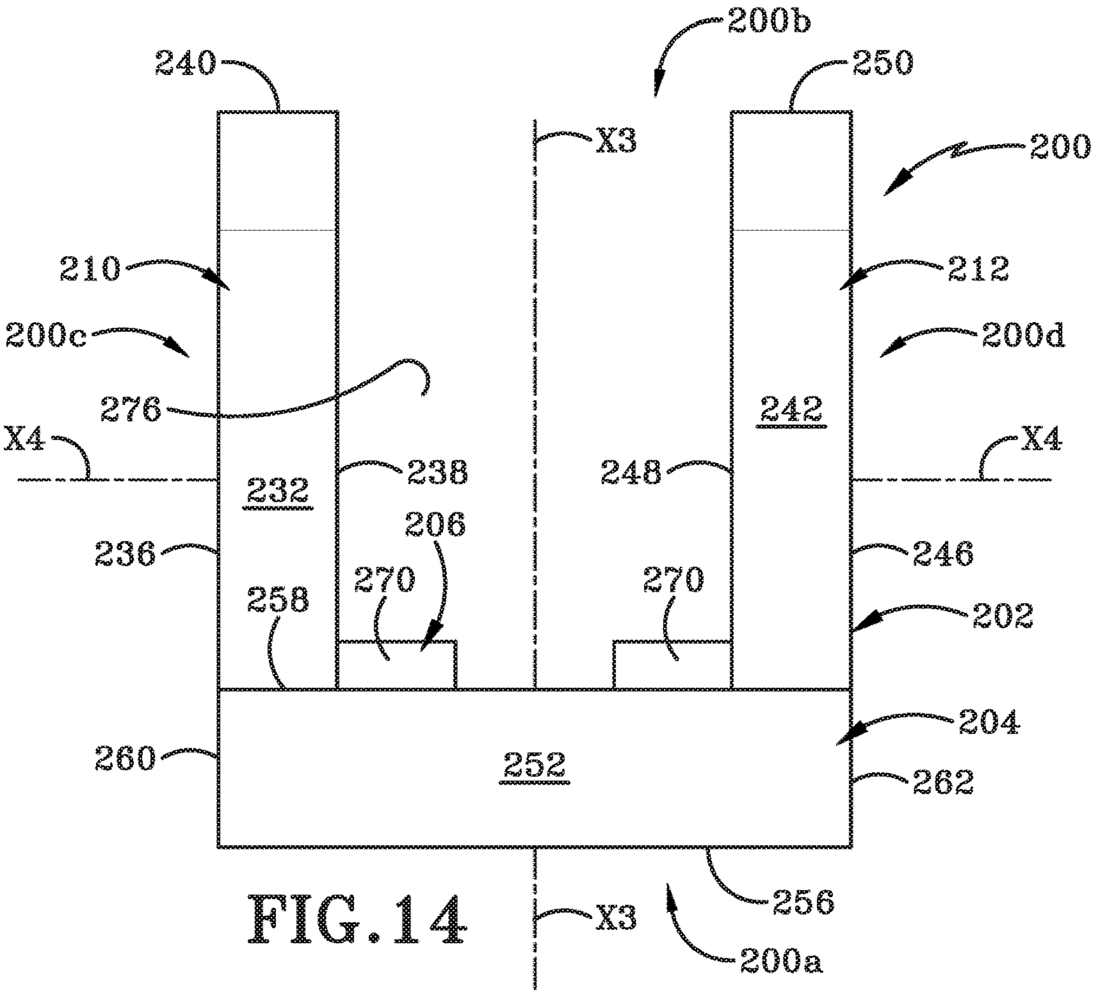
FIG. 14 is a top elevation view of the airway management device of FIG. 12.
Figure 15:
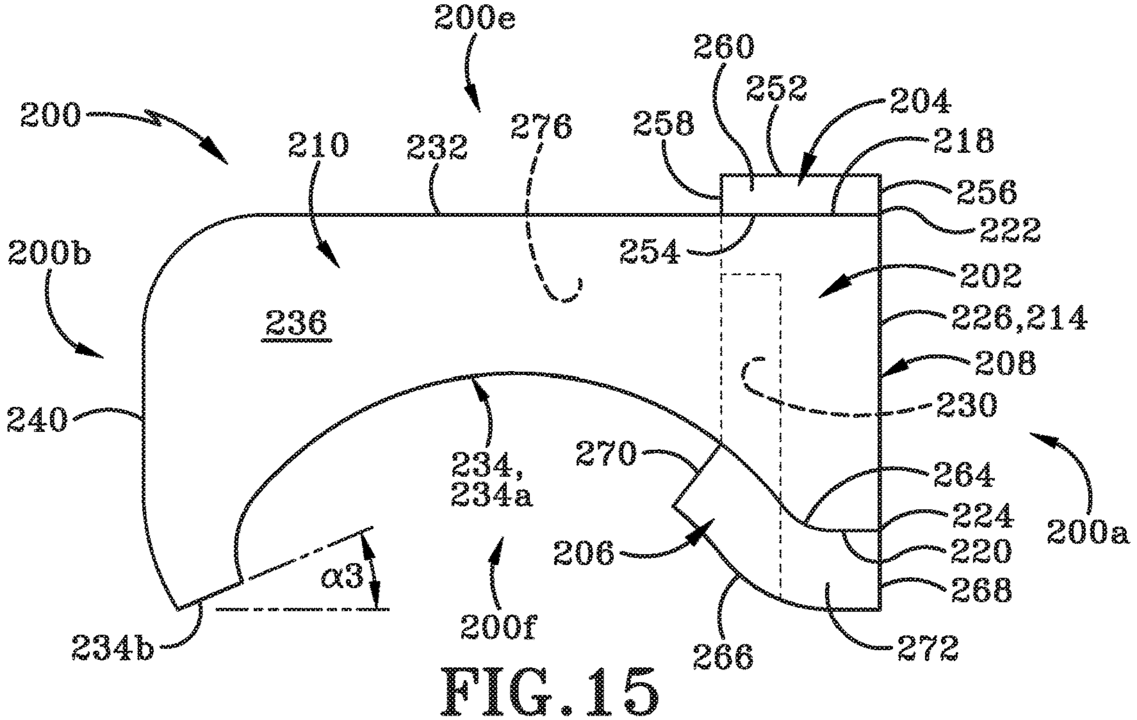
FIG. 15 is a side elevation view of the airway management device of FIG. 12.

With reference to FIG. 6 through FIG. 11E, the airway management device 1000 is configurable between a neutral, stored, or non-deployed position 1012 (FIG. 6) and a deployed position 1014 (FIG. 11D). When the airway management device 1000 is viewed in the neutral position 1012, the airway management device 1000 includes a front end 1010*a*, a rear end 1010*b*, a first side 1010*c*, a second side 1010*d*, and a top 1010*e* and a bottom 1010*f*. The front end 1010*a* and the rear end 1010*b* define a longitudinal direction therebetween. The first side 1010*c* and the second side 1010*d* define a transverse direction therebetween. The top 1010*e* and the bottom 1010*f* define a vertical direction therebetween.

The airway management device 1000 includes a longitudinal central axis X1' extending from the front end 1010*a* to the rear end 1010*b* and a transverse central axis X2' extending from the first side 1010*c* to the second side 1010*d*. The disclosure may make reference to certain components, walls, sides, surfaces, points and the like as being outer or inner which may respectively mean facing generally toward or away from the longitudinal central axis X1' or the transverse central axis X2'. Components, walls, sides, surfaces, points and the like referenced as outer generally face away from the longitudinal central axis X1' or the transverse central axis X2' and components, walls, sides, surfaces, points and the like referenced as inner generally face toward the longitudinal central axis X1' or the transverse central axis X2'.

With primary reference to FIG. 6 through FIG. 10, the airway management device 1000 includes a base 1016 having a first base portion 1018, a second base portion 1020, a pressure block 1022, a rear wall 1024, and an aperture 1028 defined by the second base portion 1020 in the interior region 1077. The airway management device 1000 further includes a securing assembly 1030 and a fastening assembly 1032.

The first base portion 1018 includes a top wall 1034, a bottom wall 1036, a first outer wall 1038, a second outer wall 1040, a third outer wall 1042, a fourth outer wall 1044, a fifth outer wall 1046, a first inner wall 1048, a second inner wall 1050, a third inner wall 1052, and a pivot axis XP1' (FIG. 11C). In one example, the pivot axis XP1' is a living hinge; however, it is to be understood that the pivot axis XP1' may be any suitable pivot axis. The first base portion 1018 is substantially U-shaped in configuration and is integrally connected to the second base portion 1020 via the living hinge. The second base portion 1020 nests inside an opening 1053 defined in the substantially U-shaped first base portion 1018 when the first base portion 1018 is in the neutral position.

Figure 6:
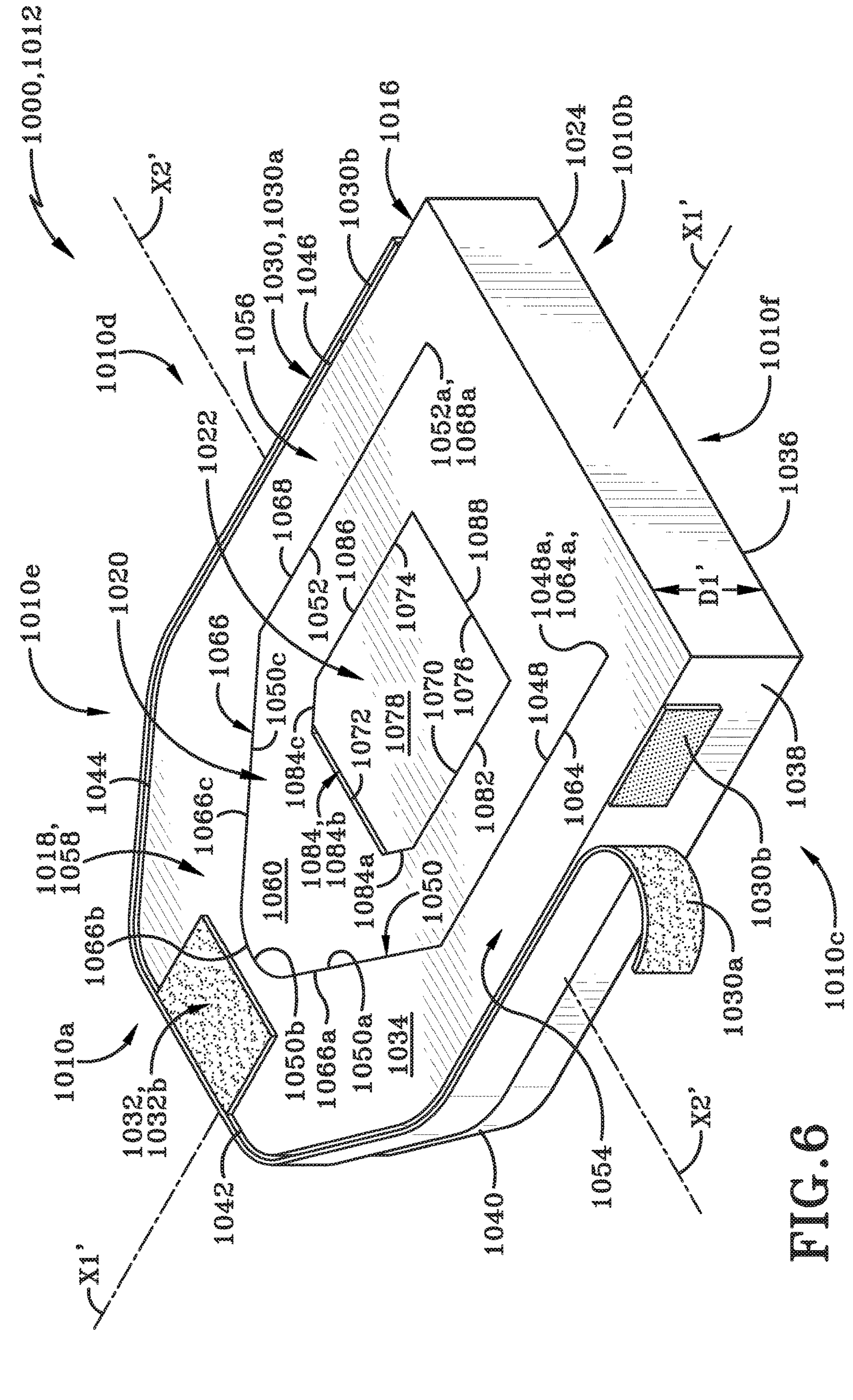
FIG. 6 is a rear top side perspective view of a second embodiment of an airway management device in accordance with one aspect of the present disclosure.
Figure 7:
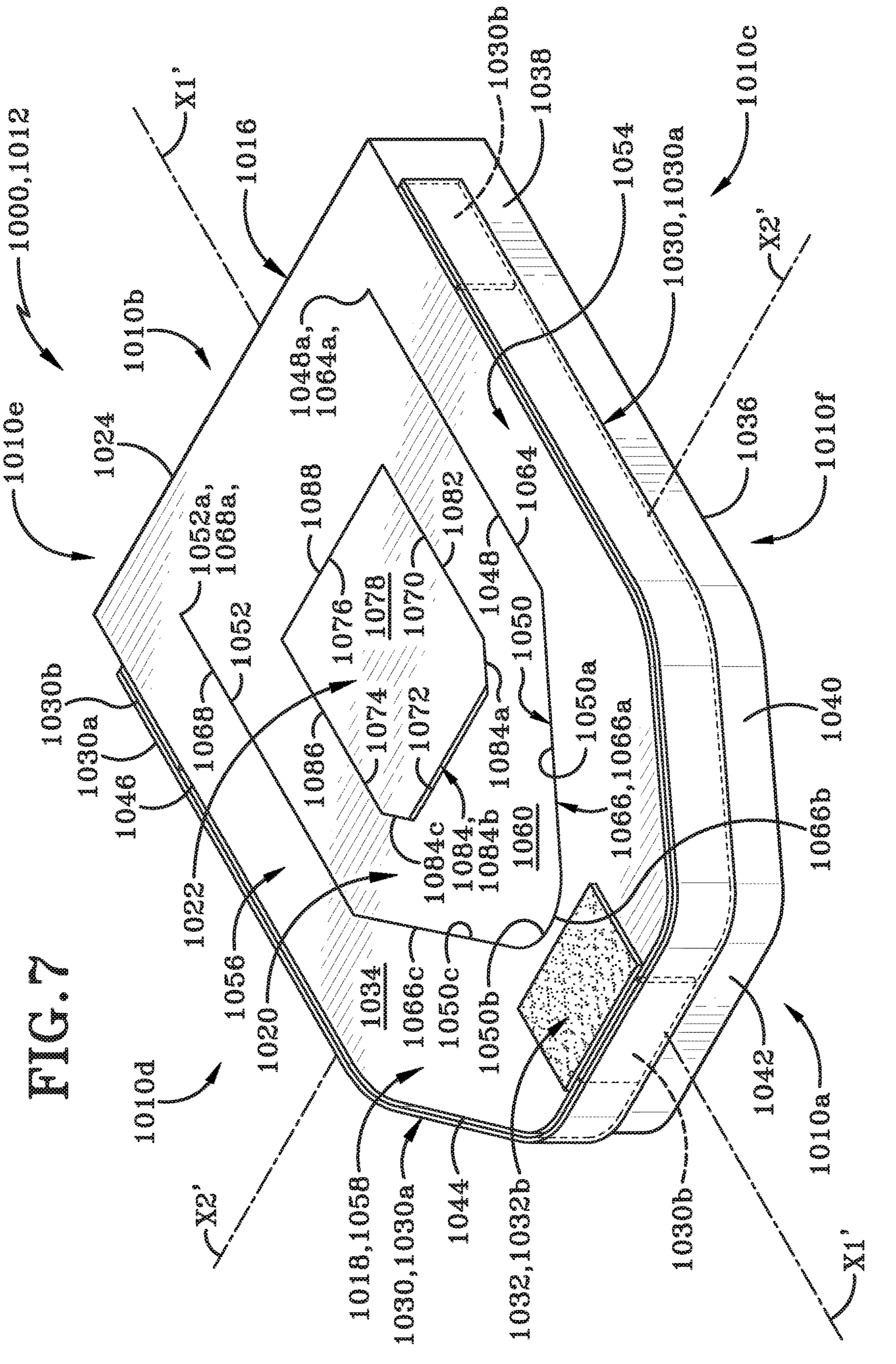
FIG. 7 is a front top side perspective view of the airway management device of FIG. 6.

As shown in FIG. 6, the top wall 1034 is spaced a distance D1' from the bottom wall 1036. In one example, the distance D1' is approximately 2 inches; however, the distance D1' may be any suitable distance.

With reference to FIG. 6 through FIG. 10, the first outer wall 1038 is positioned between the top wall 1034, the bottom wall 1036, the rear wall 1024, and the second outer wall 1040. The second outer wall 1040 is positioned between the top wall 1034, the bottom wall 1036, the third outer wall 1042, and the first outer wall 1038. The third outer wall 1042 is positioned between the top wall 1034, the bottom wall 1036, the fourth outer wall 1044 and the second outer wall 1040. The fourth outer wall 1044 is positioned between the top wall 1034, the bottom wall 1036, the fifth outer wall 1046, and the third outer wall 1042. The fifth outer wall 1046 is positioned between the top wall 1034, the bottom wall 1036, the rear wall 1024, and the fourth outer wall 1044.

With continued reference to FIG. 6-FIG. 10, the first outer wall 1038 extends generally longitudinally from the rear wall 1024 to the second outer wall 1040 a distance D2'. In one example, the distance D2' is approximately 9 inches; however, the distance D2' may be any suitable distance. The second outer wall 1040 extends generally at an angle α1' from the first outer wall 1038 to the third outer wall 1042. In one example, the angle α1' is approximately 143 degrees relative to the first outer wall 1038; however, the angle α1' may be any suitable angle. The third outer wall 1042 extends generally transversely from the second outer wall 1040 to the fourth outer wall 1044. The fourth outer wall 1044 extends generally at an angle α2' from the third outer wall 1042 to the fifth outer wall 1046. In one example, the angle α2' is approximately 143 degrees relative to the fifth outer wall 1046; however, the angle α2' may be any suitable angle. The fifth outer wall 1046 extends generally longitudinally from the fourth outer wall 1044 to the rear wall 1024 a distance D3'. In one example, the distance D3' is approximately 9 inches; however, the distance D3' may be any suitable distance.

With continued reference to FIG. 6-FIG. 10, the first outer wall 1038 is generally parallel with the fifth outer wall 1046 and the third outer wall 1042 is generally parallel with the rear wall 1024. The first inner wall 1048 is generally parallel to the first outer wall 1038 and is spaced a distance D4' from the first outer wall 1038. In one example, the distance D4' is approximately 1.5 inches; however the distance D4' may be any suitable distance. The first inner wall 1048 is positioned between the rear wall 1024 and the second inner wall 1050. The first inner wall 1048 includes a rear end 1048*a* spaced a distance D5' from the rear wall 1024. In one example, the distance D5' is approximately 1.5 inches; however, the distance D5' may be any suitable distance. The first inner wall 1048 extends longitudinally from the rear end 1048*a* to the second inner wall 1050 a distance D6'. In one example, the distance D6' is approximately 6 inches; however, the distance D6' may be any suitable distance.

With continued reference to FIG. 6-FIG. 10, the second inner wall 1050 is positioned between the first inner wall 1048 and the third inner wall 1052. The second inner wall 1050 includes a first portion 1050*a*, a second portion 1050*b*, and a third portion 1050*c*. The first portion 1050*a* extends at an angle α3' from the first inner wall 1048 to the second portion 1050*b*. In one example, the angle α3' is approximately 142 degrees relative to the first inner wall 1048; however, the angle α3' may be any suitable angle. The second portion 1050*b* extends generally in an arcuate manner between the first portion 1050*a* and the third portion 1050*c*. The third portion 1050*c* extends at an angle α4' from the third inner wall 1052 to the second portion 1050*b*. In one example, the angle α4' is approximately 142 degrees relative to the third inner wall 1052; however, the angle α4' may be any suitable angle. A front most point on the second portion 1050*b* is spaced a distance D7' from the rear wall 1024. In one example, the distance D7' is approximately 11 inches; however, the distance D7' may be any suitable distance. A transverse outermost point of the first portion 1050*a* is spaced a distance D8' from a transverse outermost point of the third portion 1050*c*. In one example, the distance D8' is approximately 6.5 inches; however, the distance D8' may be any suitable distance.

With continued reference to FIG. 6-FIG. 10, the third inner wall 1052 is generally parallel to the fifth outer wall 1046 and may be spaced a distance D9' from the fifth outer wall 1046. In one example, the distance D9' is approximately 1.5 inches; however the distance D9' may be any suitable distance. The third inner wall 1052 is positioned between the rear wall 1024 and the second inner wall 1050. The third inner wall 1052 includes a rear end 1052*a* spaced a distance D10' from the rear wall 1024. In one example, the distance D10' is approximately 1.5 inches; however, the distance D10' may be any suitable distance. The third inner wall 1052 extends generally longitudinally from the rear end 1052*a* to the second inner wall 1050 a distance D11'. In one example, the distance D11' is approximately 6 inches; however, the distance D11' may be any suitable distance.

Figure 8:
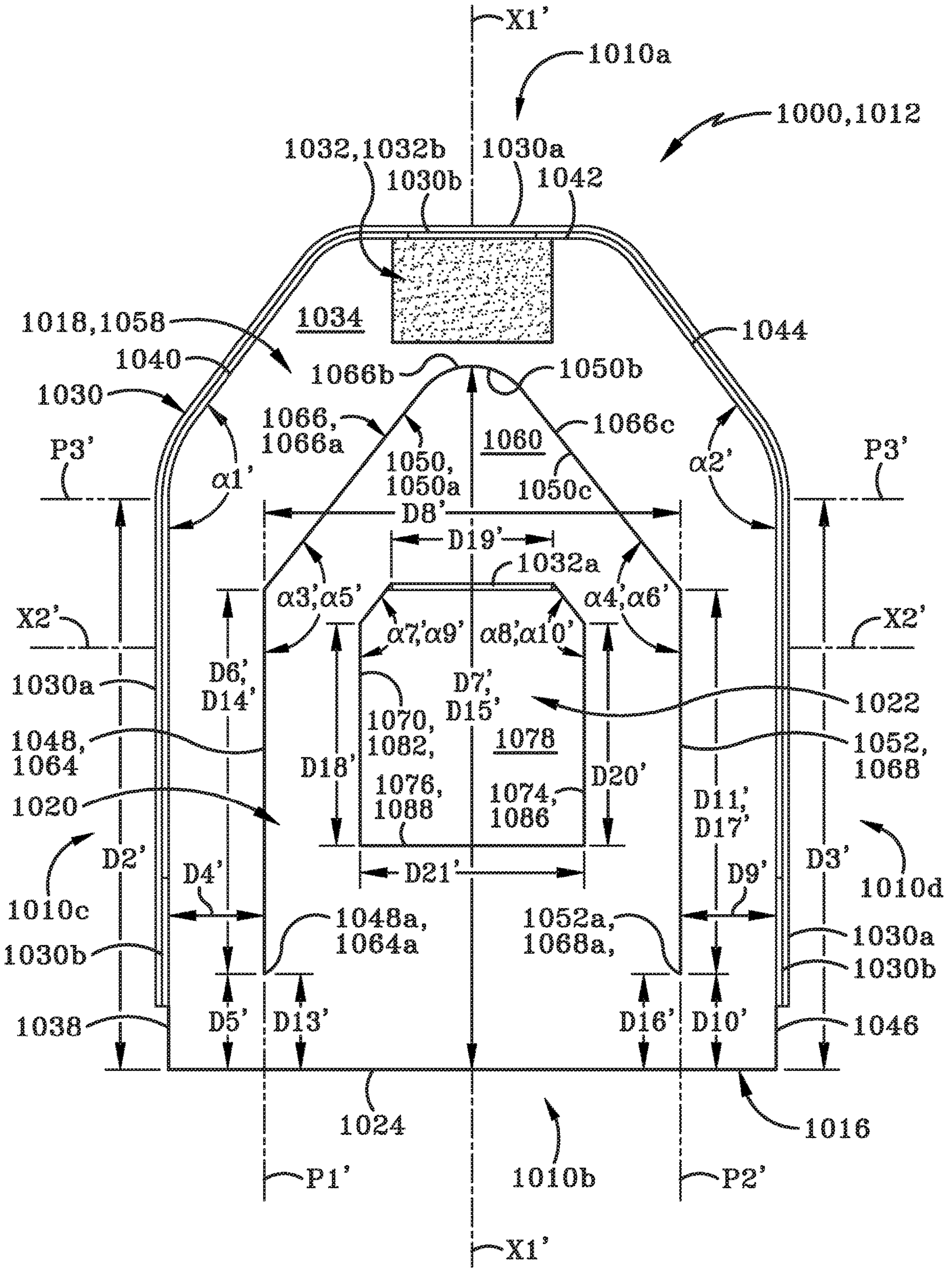
FIG. 8 is a top elevation view of the airway management device of FIG. 6.
Figures 9, 10:
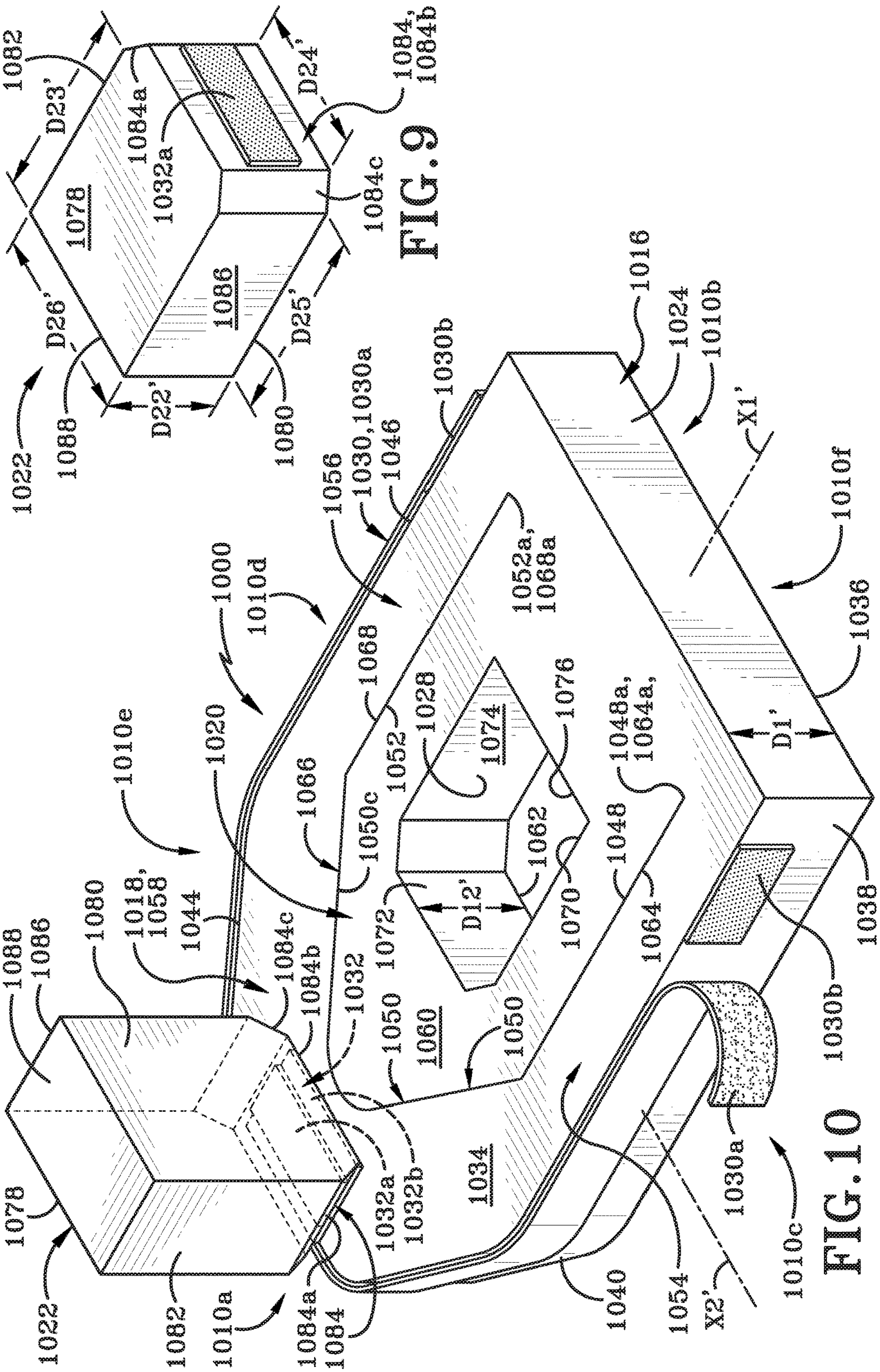
FIG. 9 a front top side perspective view of a pressure block.
FIG. 10 is a a rear top side perspective view of an airway management device with a pressure block operably engaged with the first base portion.

With reference to primary reference to FIG. 8, and when the airway management device 1000 is in the neutral position 1012, the airway management device 1000 further includes an imaginary vertical longitudinally extending first plane P1' defined by the first inner wall 1048, an imaginary vertical longitudinally extending second plane P2' defined by the third inner wall 1052, and an imaginary vertical transversely extending third plane P3' defined by a connection point of the first outer wall 1038 and the second outer wall 1040. The first base portion 1018 includes a first base arm 1054, a second base arm 1056 and an engaging portion 1058. As shown in FIG. 8, and when the airway management device 1000 is in the neutral position 1012, the first base arm 1054 is formed by and bounded by the top wall 1034, the bottom wall 1036, the first outer wall 1038, the first inner wall 1048, the rear wall 1024, at least portion of the first plane P1', and at least a portion of the second plane P2'. When the airway management device 1000 is in the neutral position 1012, the second base arm 1056 is formed by and bounded by the top wall 1034, the bottom wall 1036, the fifth outer wall 1046, the third inner wall 1052, the rear wall 1024, at least a portion of the second plane P2', and at least a portion of the third plane P3'. When the airway management device 1000 is in the neutral position 1012, the engaging portion 1058 may be formed by and bounded by the top wall 1034, the bottom wall 1036, the second outer wall 1040, the third outer wall 1042, the fourth outer wall 1044, the second inner wall 1050, and at least a portion of the third plane P3'.

The rear end 1048*a* of the first inner wall 1048 and the rear end 1052*a* of the third inner wall 1052 define the pivot axis XP1' (FIG. 11C). The airway management device 1000 is configurable between the neutral position 1012 and the deployed position 1014 (FIG. 11C) by pivoting the first base portion 18 about the pivot axis XP1'. Specifically, the first base arm 1054, the second base arm 1056, and the engaging portion 1058 are rotated about the pivot axis XP1' as more fully described below.

With continued reference to FIG. 6-FIG. 10, the second base portion 20 includes a top wall 1060, a bottom wall 1062, a first outer wall 1064, a second outer wall 1066, a third outer wall 1068, a first inner wall 1070, a second inner wall 1072, a third inner wall 1074, a fourth inner wall 1076, and an interior region 1077. The top wall 1060 is spaced a distance D12' (FIG. 9) from the bottom wall 1062. In one example, the distance D12' is approximately 2 inches; however, the distance D12' may be any suitable distance.

With continued reference to FIG. 6-FIG. 10, the first outer wall 1064 is generally positioned between the top wall 1060, the bottom wall 1062, the rear wall 1024 and the second outer wall 1066. The second outer wall 1066 is generally positioned between the top wall 1060, the bottom wall 1062, first outer wall 1064, and the third outer wall 1068. The third outer wall 1068 is generally positioned between the top wall 1060, the bottom wall 1062, the rear wall 1024 and the second outer wall 1066.

The first outer wall 1064 includes a rear end 1064*a* spaced a distance D13' from the rear wall 1024. In one example, the distance D13' is approximately 1.5 inches; however, the distance D13' may be any suitable distance. The first outer wall 1064 extends longitudinally from the rear end 1064*a* to the second outer wall 1066 a distance D14'. In one example, the distance D14' is approximately 6 inches; however, the distance D14' may be any suitable distance. When the airway management device 1000 is in the neutral position 1012, the first inner wall 1048 of the first base portion 1018 is proximate to and generally parallel with the first outer wall 1064 of the second base portion 1020. As such, the distance D6' is equal to the distance D14'; however, the distance D6' and the distance D14' may be different distances.

The second outer wall 1066 is positioned between the first outer wall 1064 and the third outer wall 1068, The second outer wall 1066 includes a first portion 1066*a*, a second portion 1066*b*, and a third portion 1066*c*. The first portion 1066*a* extends at an angle α5' from the first outer wall 1064 to the second portion 1066*b*. In one example, the angle α5' is approximately 142 degrees relative to the first outer wall 1064; however, the angle α5' may be any suitable angle. The second portion 1066*b* extends generally in an arcuate manner between the first portion 1066*a* and the third portion 1066*c*. The third portion 1066*c* extends at an angle α6' from the third outer wall 1068 to the second portion 1066*b*. In one example, the angle α6' is approximately 142 degrees relative to the third outer wall 1068; however, the angle α6' may be any suitable angle. A front most point on the second portion 1066*b* is spaced a distance D15' from the rear wall 1024. In one example, the distance D15' is approximately 11 inches; however, the distance D15' may be any suitable distance. When the airway management device 1000 is in the neutral position 1012, the second inner wall 1050 of the first base portion 1018 is proximate to and complementary in shape to the second outer wall 1066 of the second base portion 1020. As such, the distance D7' is equal to the distance D15'; however, the distance D7' and the distance D15' may be different distances.

The third outer wall 1068 includes a rear end 1068*a* spaced a distance D16' from the rear wall 1024. In one example, the distance D16' is approximately 1.5 inches; however, the distance D16' may be any suitable distance. The third outer wall 1068 extends generally longitudinally from the rear end 1068*a* to the second outer wall 1066 a distance D17'. In one example, the distance D17' is approximately 6 inches; however, the distance D17' may be any suitable distance. When the airway management device 1000 is in the neutral position 1012, the third inner wall 1052 of the first base portion 1018 is proximate to and generally parallel with the third outer wall 1068 of the second base portion 1020. As such, the distance D11' is equal to the distance D17'; however, the distance D11' and the distance D17' may be different distances.

When the airway management device 1000 is in the neutral position 1012, the first outer wall 1064 is generally longitudinally aligned with the first plane P1' and the third outer wall 1068 is generally longitudinally aligned with the second plane P2'. The top wall 1060 is bounded by the first outer wall 1060, the second outer wall 1062, the third outer wall 1064, the first inner wall 1070, the second inner wall 1072, the third inner wall 1074, the fourth inner wall 1076, the first plane P1' and the third plane P3'.

The first inner wall 1070 is generally positioned between the top wall 1060, the bottom wall 1062, the second inner wall 1072 and the fourth inner wall 1076. The second inner wall 1072 is generally positioned between the top wall 1060, the bottom wall 1062, the first inner wall 1070 and the third inner wall 1074. The third inner wall 1074 is generally positioned between the top wall 1060, the bottom wall 1062, the second inner wall 1072, and the fourth inner wall 1076. The fourth inner wall 1076 is generally positioned between the top wall 1060, the bottom wall 1062, the first inner wall 1070 and the third inner wall 1074. The first inner wall 1070 extends generally longitudinally from the fourth inner wall 1076 to the second inner wall 1072 a distance D18'. In one example, the distance D18' is approximately 3.5 inches; however, the distance D18' may be any suitable distance.

The second inner wall 1072 includes a first portion 1072*a*, a second portion 1072*b*, and a third portion 1072*c*. The first portion 1072*a* extends at an angle α7' from the first inner wall 1070 to the second portion 1072*b*. In one example, the angle α7' is approximately 142 degrees relative to the first inner wall 1070; however, the angle α7' may be any suitable angle. The second portion 1072*b* is generally parallel with the fourth inner wall 1076 and extends generally transversely between the first portion 1072*a* and the third portion 1072*c*. The third portion 1072*c* extends at an angle α8' from the third inner wall 1074 to the second portion 1072*b*. In one example, the angle α8' is approximately 142 degrees relative to the third inner wall 1074; however, the angle α8' may be any suitable angle. The second portion 1072*b* extends generally transversely between the first portion 1072*a* and the third portion 1072*c* a distance D19'. In one example, the distance D19' is approximately 2.5 inches; however, the distance D19' may be any suitable distance. The third inner wall 1074 extends generally longitudinally from the second inner wall 1072 to the fourth inner wall 1076 a distance D20'. In one example, the distance D20' is approximately 3.5 inches; however, the distance D20' may be any suitable distance. The fourth inner wall 1076 extends generally transversely from the third inner wall 1074 to the first inner wall 1070 a distance D21'. In one example, the distance D21' is approximately 3.5 inches; however, the distance D21' may be any suitable distance. Further, the first inner wall 1070 is generally parallel to and generally faces the third inner wall 1074 and the second portion 1072*b* of the second inner wall 1072 is generally parallel to and generally faces the fourth inner wall 1076.

With continued reference to FIG. 6-FIG. 10, the first inner wall 1070, the second inner wall 1072, the third inner wall 1074, and the fourth inner wall 1076 define the aperture 1028 which extends vertically through the base 1016.

With continued reference to FIG. 6-FIG. 10, the pressure block 22 includes a top wall 1078, a bottom wall 1080, a first outer wall 1082, a second outer wall 1084, a third outer wall 1086, and a fourth outer wall 1088. The top wall 1078 is spaced a distance D22' from the bottom wall 1080. In one example, the distance D22' is approximately 2 inches; however, the distance D22' may be any suitable distance. The first outer wall 1082 is generally positioned between the top wall 1078, the bottom wall 1080, the second outer wall 1084, and the fourth outer wall 1088. The second outer wall 1084 is generally positioned between the top wall 1078, the bottom wall 1080, the third outer wall 1086 and the first outer wall 1082. The third outer wall 1086 is generally positioned between the top wall 1078, the bottom wall 1080, the fourth outer wall 1088, and the second outer wall 1084. The fourth outer wall 1088 is generally positioned between the top wall 1078, the bottom wall 1080, the first outer wall 1082 and the third outer wall 1086.

The first outer wall 1082 extends generally longitudinally from the fourth outer wall 1088 to the second outer wall 1084 a distance D23'. In one example, the distance D23' is approximately 3.5 inches; however, the distance D23' may be any suitable distance. The second outer wall 1084 includes a first portion 1084*a,* a second portion 1084*b,* and a third portion 1084*c*. The first portion 1084*a* extends at an angle α9' from the first outer wall 1082 to the second portion 1084*b*. In one example, the angle α9' is approximately 142 degrees relative to the first outer wall 1082; however, the angle α9' may be any suitable angle. The second portion 1084*b* is generally parallel with the fourth outer wall 1088 and extends generally transversely between the first portion 1084*a* and the third portion 1084*c*. The third portion 1084*c* extends at an angle α10' from the third outer wall 1086 to the second portion 1084*b*. In one example, the angle α10' is approximately 142 degrees relative to the third outer wall 1086; however, the angle α10' may be any suitable angle. The second portion 1084*b* extends generally transversely between the first portion 1084*a* and the third portion 1084*c* a distance D24'. In one example, the distance D24' is approximately 2.5 inches; however, the distance D24' may be any suitable distance. The third outer wall 1086 extends generally longitudinally from the second outer wall 1084 to the fourth outer wall 1088 a distance D25'. In one example, the distance D25' is approximately 3.5 inches; however, the distance D25' may be any suitable distance. The fourth outer wall 1088 extends generally transversely from the third outer wall 1086 to the first outer wall 1082 a distance D26'. In one example, the distance D26' is approximately 3.5 inches; however, the distance D26' may be any suitable distance. Further, the first outer wall 1082 is generally parallel to and generally faces the third outer wall 1086 and the second portion 1084*b* of the second outer wall 1084 is generally parallel to and generally faces the fourth outer wall 1088.

When the airway management device 1000 is in the neutral position 1012, the pressure block 1022 is configured to be operationally engaged with the base 1016. In one example, the pressure block 1022 is releasably held within the aperture 1028 via an interference fit between the first outer wall 1082, the second outer wall 1084, the third outer wall 1086, and the fourth outer wall 1088 of the pressure block 1022 and the first inner wall 1070, the second inner wall 1072, the third inner wall 1074, and the fourth inner wall 1076 of the second base portion 1020 near the interior region 1077.

With continued reference to FIG. 6-FIG. 10, the securing assembly 1030 includes a securing member 1030*a* and a plurality of securing points 1030*b*. In one embodiment, the securing member 1030*a* is a strap including hooks and the plurality of securing points 1030*b* are patches of material including loops; however, it is to be understood that the securing member 1030*a* could alternatively be a strap including loops and the plurality of securing points 1030*b* could be patches of material including hooks.

In one example, the securing assembly 1030 includes eight securing points 1030*b* where one securing point 1030*b* is provided on the first outer wall 1038 of the first base portion 1818 proximate the top wall 1034 and the rear wall 1024, one securing point 1030*b* is provided on the first outer wall 1038 proximate the top wall 1034 and the second outer wall 1040, one securing point 1030*b* is provided on the second outer wall 1040 proximate the top wall 1034 and the third outer wall 1042, one securing point 1030*b* is provided on the third outer wall 1042 proximate the top wall 1034 and the fourth outer wall 1044, one securing point 1030*b* is provided on the fourth outer wall 1044 proximate the top wall 1034 and the third outer wall 1042, one securing point 1030*b* is provided on the fifth outer wall 1046 proximate the top wall 1034 and the fourth outer wall 1044, and one securing point 1030*b* is provided on the fifth outer wall 1046 proximate the top wall 1034 and the rear wall 1024. When the airway management device 1000 is viewed in the neutral position 1012, the securing member 1030*a* (i.e., the strap) is operably engaged with the securing points 1030*b* such that the securing member 1030*a* is operably engaged with the first outer wall 1038, the second outer wall 1040, the third outer wall 1042, the fourth outer wall 1044, and the fifth outer wall 1046 proximate the top wall 1034. The securing member 1030*a* and the plurality of securing points 1030*b* may be any suitable size.

Although particular positions of the securing points 1030*b* have been described, it is to be understood that the securing points 1030*b* may be provided in any suitable locations. Further, although the securing assembly 1030 has been described as having a hook and loop engagement mechanism, it is to be understood that the securing assembly 1030 may utilize any suitable securing mechanisms, including, but not limited to, adhesives or mechanical connections.

In one embodiment the fastening assembly 1032 includes a fastening mechanism 1032*a* and at least one fastening point 1032*b*. In one example, the fastening mechanism 1032*a* is a patch of material including hooks and the at least one fastening point 1032*b* is a patch of material including loops; however, it is to be understood that the fastening mechanism 1032*a* could alternatively be a patch of material including loops and the at least one fastening point 1032*b* could be a patch of material including hooks. The fastening mechanism 1032*a* (i.e., the patch of material including hooks) is provided on the second portion 1084*b* of the second outer wall 1084 of the pressure block 1022 and the at least one fastening point 1032*b* is provided on the top wall 1034 of the engaging portion 1058 of the first base portion 1018 proximate the third outer wall 1042. The pressure block 1022 is operably engaged with the engaging portion 1058 of the first base portion 1018 by releasably securing the fastening mechanism 1032*a* to the at least one fastening point 1032*b* as further described below. The fastening mechanism 1032*a* and the at least one fastening point 1032*b* may be any suitable size.

Although a particular position of the fastening mechanism 1032*a* and the at least one fastening point 1032*b* have been described, it is to be understood that the fastening mechanism 1032*a* and the at least one fastening point 1032*b* may be provided in any suitable location. Further, although the fastening assembly 1032 has been described as having a hook and loop engagement mechanism, it is to be understood that the fastening assembly 1032 may utilize any suitable fastening mechanisms, including, but not limited to, adhesives or mechanical fasteners.

With primary reference to FIG. 11A through FIG. 11E, and in operation, the airway management device 1000 may be utilized by a person 100 to restore and/or maintain a patent airway. The airway management device 1000 is placed on a surface 101. The airway management device 1000 is configurable between a neutral position 1012 (FIG. 11A) and a deployed position 1014 (FIG. 11C and FIG. 11D) to support various portions of a person's 100 head 102.

In operation, the pressure block 1022 is removed from the aperture 1028 and releasably secured to the first base portion 1018. Specifically, and in one example, the fastening mechanism 1032*a* (i.e., the patch including hooks, which, in an alternative embodiment, may include loops instead of hooks which may be connected to hooks in a separate component) provided on the second portion 1084*b* of the second outer wall 1084 of the pressure block 1022 is operably engaged with the fastening point 1032*b* provided on the top wall 1034 of the engaging portion 1058 (FIG. 11A) of the first base portion 1018.

As shown in FIG. 11A, when the person 100 is in the supine position, the second base portion 1020 supports an occipital region 104 of the person's head 102 and a neck region 106 of the person 100. In one example, at least a portion of the occipital region 104 of the head 102 of the person 100 is received within the aperture 1028 and at least a portion of the occipital region 104 of the head 102 of the person 100 and the neck region 106 of the person 100 are supported by the top wall 1060, the first inner wall 1070, the second inner wall 1072, the third inner wall 1074, and the fourth inner wall 1076 between the first plane P1' and the second plane P2'.

In operation, and as shown in FIG. 11B, the first base portion 1018 is rotated about the pivot axis XP1' over a face 108 of the person 100 in a direction generally indicated by arrow A. In one example, an operator (not shown) may grasp at least a portion of the second portion 1050*b* of the second inner wall 1050 to aid in rotating the first base portion 1018 about the pivot axis XP1'. As shown in FIG. 11B, the bottom wall 1036 of the first base portion 1018 contacts a chin and posterior mandibular region 110 of the person 100 and the fourth outer wall 1088 of the pressure block 1022 contacts a chest region 112 of the person 100.

As shown in FIG. 11C, the securing assembly 1030 provides a force in a direction indicated generally by arrow B. As shown in FIG. 11C, the force provided by the securing assembly 1030 compresses the pressure block 1022 in a direction generally indicated by arrow C. The pressure block 1022 and the first base portion 1018 provide a force to the chin and posterior mandibular region 110 of the person 100 in a general direction indicated by arrow D which aligns the axes of a mouth 114, pharynx (not shown) and larynx (not shown) of the person 100 into alignment. The alignment of the axes may also be referred to as a "sniffing position." The sniffing position opens up the airway of the person 100 by lifting a tongue (not shown) away from the back of a throat (not shown) of the person 100.

Although the airway management device 1000 has been described as having various components operably engaged with one another in a particular manner, it is to be understood that some components may be integrally formed with the airway management device 1000 while other components are separate from yet operably engaged with the airway management device 1000. For example, and not meant as a limitation, instead of the first base portion 1018, which includes the first base arm 1054, the second base arm 1056, and the engaging portion 1058, is integrally formed with the airway management device 1000, it is entirely possible that the first base portion 1018 may be operably engaged by connecting the first base portion 1018 to the second base portion 1020 in any suitable manner. In another non-limiting example, instead of the pressure block 1022 being operably engaged with the first base portion 1018 via the fastening assembly 1032, it is to be understood that the pressure block 1022 may be integrally formed with the first base portion 1018.

A method of airway management includes providing a base including a first base portion and a second base portion, placing the base on a surface, placing a person's head on the base, pivoting the first base portion from a neutral position to a deployed position, applying pressure to a person's chin with the first base portion, and lifting the person's chin so that a person's airway is unobstructed. When the first base portion is in the neutral position, the first base portion and the second base portion are aligned in a plane; and wherein when the first base portion is in the deployed position, the first base portion is aligned at an angle relative to the second base portion. In one example, the angle is an obtuse angle.

The method further includes applying pressure to a person's chest via a pressure block extending outwardly from the first base portion. When the first base portion is in the neutral position, the pressure block extends perpendicular to the plane. The method further includes detaching the pressure block from an interior region of the second base portion, and operably engaging the pressure block with the first base portion.

The method further includes compressing the pressure block via a securing assembly. In one example, the securing assembly is a removable strap.

The method further includes positioning a first base arm on one side of the person's head and positioning a second base arm on the other side of the person's head. The method further includes positioning the person's head within an aperture defined in the second base portion.

Referring to FIG. 12-FIG. 16B, there is shown a third embodiment of an airway management device in accordance with one aspect of the present disclosure, with the airway management device generally indicated at 200. The airway management device 200 is configured to contact and provide various forces against a person's body as further described below. As such, and in one example, the airway management device 200 is made out of polyurethane foam to conform to the person's body and provide comfortability while providing suitable forces against the person's body. The airway management device 200 is made out of polyurethane foam having a density of 1.8 pounds per cubic foot; however, the airway management device 200 may be made of polyurethane foam having any suitable density. It is to be further understood that the airway management device 200 may be made out of any suitable materials.

With reference to FIG. 12 through FIG. 16B, the airway management device 10 includes a front end 200*a* and a rear end 200*b* defining a longitudinal direction therebetween, a first side 200*c* and a second side 200*d* defining a transverse direction therebetween, and a top 200*e* and a bottom 200*f* defining a vertical direction therebetween. The airway management device 200 includes a longitudinal central axis X3 extending from the front end 200*a* to the rear end 200*b* and a transverse central axis X4 extending from the first side 200*c* to the second side 200*d*. The disclosure may make reference to certain components, walls, sides, surfaces, points and the like as being outer or inner which may respectively mean facing generally toward or away from the longitudinal central axis X3 or the transverse central axis X4. Components, walls, sides, surfaces, points and the like referenced as outer generally face away from the longitudinal central axis X3 or the transverse central axis X4 and components, walls, sides, surfaces, points and the like referenced as inner generally face toward the longitudinal central axis X3 or the transverse central axis X4.

The airway management device 200 includes a first portion 202, a second portion 204, and a third portion 206. The first portion 202 includes a front member 208, a first base portion 210, and a second base portion 212. The front member 208 includes a front wall 214, a rear wall 216, a top wall 218, a bottom wall 220, a top edge 222, a bottom edge 224, a first side edge 226, a second side edge 228, and a cavity 230.

The first base portion 210 includes a top wall 232, a bottom wall 234, an outer wall 236, an inner wall 238, and a rear wall 240. The second base portion 212 includes a top wall 242, a bottom wall 244, an outer wall 246, an inner wall 248, and a rear wall 250. The top wall 232 of the first base portion 210 extends generally longitudinally from the top edge 218 of the front member 208 to the rear wall 240 of the first base portion 210. The bottom wall 234 of the first base portion 210 includes a first bottom portion 234*a* and a second bottom portion 234*b*. The first bottom portion 234*a* extends from the bottom wall 220 of the front member 208 in a generally arcuate manner to the second bottom portion 234*b*. The second bottom portion 234*b* extends from the rear wall 240 to the first bottom portion 234*a* vertically upward at an angle α3. In one example, the angle α3 is approximately 23 degrees relative to the horizontal; however, the angle α3 may be any suitable angle. The connection between the first bottom portion 234*a* and the second bottom portion 234*b* forms a hook-like structure to aid in the operation of the airway management device 200 as further described below. The outer wall 236 extends generally longitudinally from the first side edge 222 of the front member 208 to the rear wall 240 of the first base portion 210. The inner wall 238 of the first base portion 210 extends generally longitudinally from the rear wall 216 of the front member 208. The top wall 232, the bottom wall 234, and the rear wall 240 include a thickness defined by the outer wall 236 and the inner wall 238.

The rear wall 240 of the first base portion 210 includes a top end 236*a* and a bottom end 236*b*. The top end 236*a* forms an arcuate connection with the top wall 232. The bottom end 236*b* forms an arcuate connection with the bottom wall 234.

The top wall 242 of the second base portion 212 extends generally longitudinally from the top edge 218 of the front member 208 to the rear wall 250 of the second base portion 212. The bottom wall 244 of the second base portion 212 includes a first bottom portion 244*a* and a second bottom portion 244*b*. The first bottom portion 244*a* extends from the bottom wall 220 of the front member 208 in a generally arcuate manner to the second bottom portion 244*b*. The second bottom portion 244*b* extends from the rear wall 240 to the first bottom portion 244*a* vertically upward at an angle α4. In one example, the angle α4 is approximately 23 degrees relative to the horizontal; however, the angle α4 may be any suitable angle. The connection between the first bottom portion 244*a* and the second bottom portion 244*b* forms a hook-like structure to aid in the operation of the airway management device 200 as further described below. The outer wall 246 extends generally longitudinally from the first side edge 222 of the front member 208 to the rear wall 250 of the second base portion 212. The inner wall 248 of the second base portion 212 extends generally longitudinally from the rear wall 216 of the front member 208. The top wall 242, the bottom wall 244, and the rear wall 250 includes a thickness defined by the outer wall 246 and the inner wall 248.

The rear wall 250 of the second base portion 212 includes a top end 246*a* and a bottom end 246*b*. The top end 246*a* forms an arcuate connection with the top wall 242. The bottom end 246*b* forms an arcuate connection with the bottom wall 244.

The rear wall 216 of the front member 208 defines a portion of the cavity 230. The cavity 230 is adapted to prevent tracheal compression and subsequent obstruction of the airway as well as provide comfortability to the person as further described below. The cavity 230 is positioned approximately midway between the inner wall 238 of the first base portion 210 and the inner wall 238 of the second base portion 244 and is configured to receive a portion of a person as described below.

The second portion 204 includes a top wall 252, a bottom wall 254, a front wall 256, a rear wall 258, a first side wall 260, and a second side wall 262. The second portion 204 is operably engaged with the top wall 218 of the front member 208. The front wall 256 of the second portion 204 extends vertically upwardly from the top edge 222 of the front member 208. The first side wall 260 extends vertically upward from the outer wall 236 of the first base portion 210. The second side wall 262 extends vertically upward from the outer wall 246 of the second base portion 212. The top wall 252 of the second portion 204 extends longitudinally from the front wall 256 to the rear wall 258 and transversely from the first side wall 260 to the second side wall 262. The bottom wall 254 of the second portion 204 extends longitudinally from the front wall 256 to the rear wall 258 and transversely from the first side wall 260 to the second side wall 262. The bottom wall 254 is operably engaged with the top wall 218 of the front member 208. The bottom wall 254 is operably engaged with the top wall 218 of the front member 208 with an adhesive, although other connection mechanisms may be utilized.

The third portion 206 includes a top wall 264, a bottom wall 266, a front wall 268, a rear wall 270, a first side wall 272, and a second side wall 274. The third portion 206 is operably engaged with the bottom wall 220 of the front member 208, a portion of the bottom wall 234 of the first base portion 210, and a portion of the bottom wall 244 of the second base portion 212. The front wall 268 of the third portion 206 extends vertically downward from the bottom edge 224 of the front member 208. The first side wall 272 extends vertically downward from the bottom wall 220 of the front member 208 and a portion of the bottom wall 234 of the first base portion 210. The second side wall 274 extends vertically downward from the bottom wall 220 of the front member 208 and a portion of the bottom wall 244 of the second base portion 212. The top wall 264 of the third portion 206 extends longitudinally from the front wall 268 to the rear wall 270 in an arcuate manner and transversely from the first side wall 272 to the second side wall 274. The bottom wall 266 of the third portion 206 extends longitudinally from the front wall 268 to the rear wall 270 in an arcuate manner and transversely from the first side wall 272 to the second side wall 274. The top wall 264 of the third portion 204 is operably engaged with the bottom wall 220 of the front member 208, a portion of the bottom wall 234 of the first base portion 210, and a portion of the bottom wall 244 of the second base portion 212. The top wall 264 is operably engaged with the top wall 218 of the front member 208 via an adhesive, although other connection mechanisms may be utilized.

The rear wall 270 of the third portion 206 defines a portion of the cavity 230. The cavity 230 is positioned approximately midway between the first side wall and the second side wall of the third portion 206. As stated above, the cavity 230 is configured to receive a portion of a person as described below.

The inner wall 238 of the first base portion 210, the rear wall 240 of the first base portion 210, the inner wall 248 of the second base portion 212, the rear wall 250 of the second base portion 212, the rear wall 258 of the second portion 204, the rear wall 216 of the front member 208, the rear wall 270 of the third portion 206 define an opening 276 configured to receive a portion of a person's head and neck as described below.

Figure 16A:
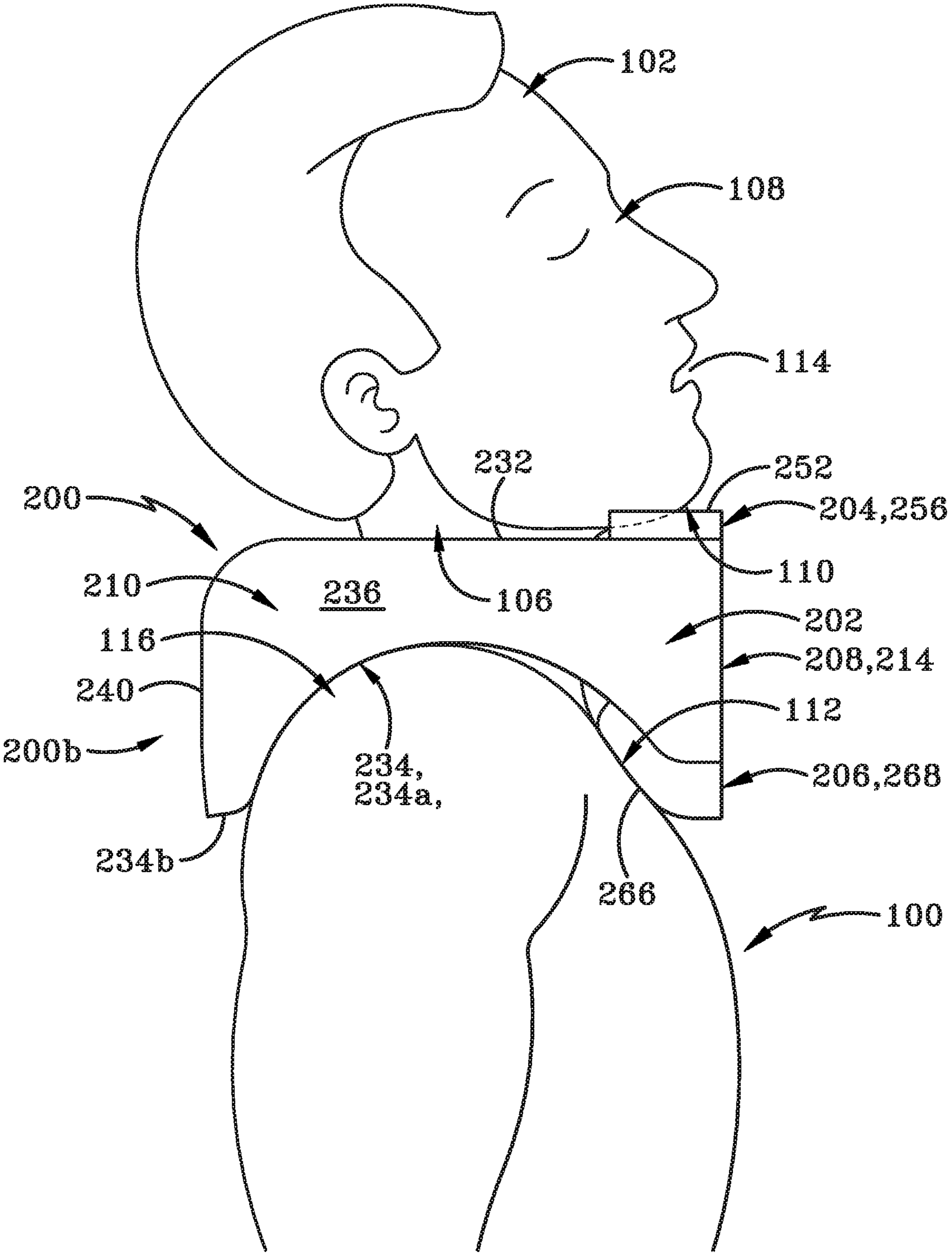
FIG. 16A is an operational view of the airway management device of FIG. 12 being utilized by a person.
Figure 16B:
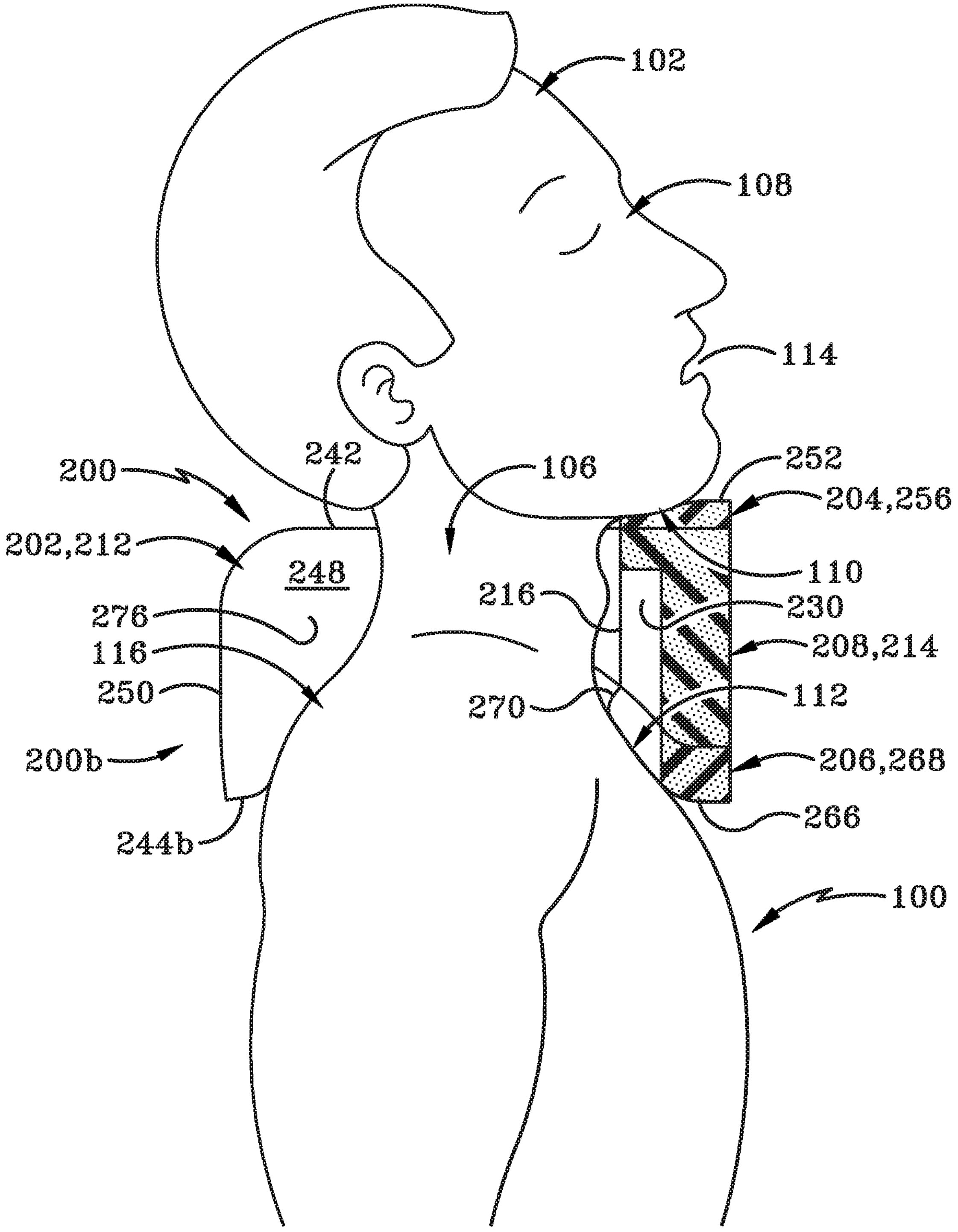
FIG. 16B is a cross section view of FIG. 16A.

With primary reference to FIG. 16A through FIG. 16B, and in operation, the airway management device 200 is utilized by a person 100 to support a head 102 and neck region 106 of the person 100.

In operation, a trachea (not shown) of the person 100 is positioned within the cavity 230 to prevent tracheal compression. The neck region 106 of the person 100 is positioned within the opening 176, the top wall 252 of the second portion 204 contacts the chin and posterior mandibular region 110 of the person 100, the bottom wall 234 of the first base portion 210 contacts a first shoulder region 116 of the person 100, the bottom wall 244 of the second base portion 212 contacts a second shoulder region not shown) of the person 100, and the bottom wall 266 of the third portion 206 contacts a chest region 112 of the person 100. As shown in FIG. 16A, the airway management device 200 supports the chin and mandibular region 110 of the person 100. Although FIG. 16A depicts the person utilizing the airway management device 200 while the person 100 is in an upright position, it is to be understood that the airway management device 200 may be utilized while the person 100 is in a sitting position and/or in a supine position.

Although the airway management device 200 has been described as having various components operably engaged with one another in a particular manner, it is to be understood that some components may be integrally formed with the airway management device 200 while other components are separate from yet operably engaged with the airway management device 200. For example, and not meant as a limitation, instead of the first portion 202, the second portion 204, and the third portion 206 being separate from yet operably engaged with one another, the first portion 202, the second portion 204, and the third portion 206 may be integrally formed with the airway management device 200.

In accordance with one aspect of the present disclosure, it is envisioned that the airway management device 200 may be utilized for supporting a neck region and chin and posterior mandibular region of a person. For example, and not meant as a limitation, the airway management device 200 may be utilized by individuals affected by sleep apnea, individuals during travel while in the sitting position, individuals having weakened shoulder and neck muscles, or by individuals having any need to support their neck region and chin and posterior mandibular region.

Figure 17:
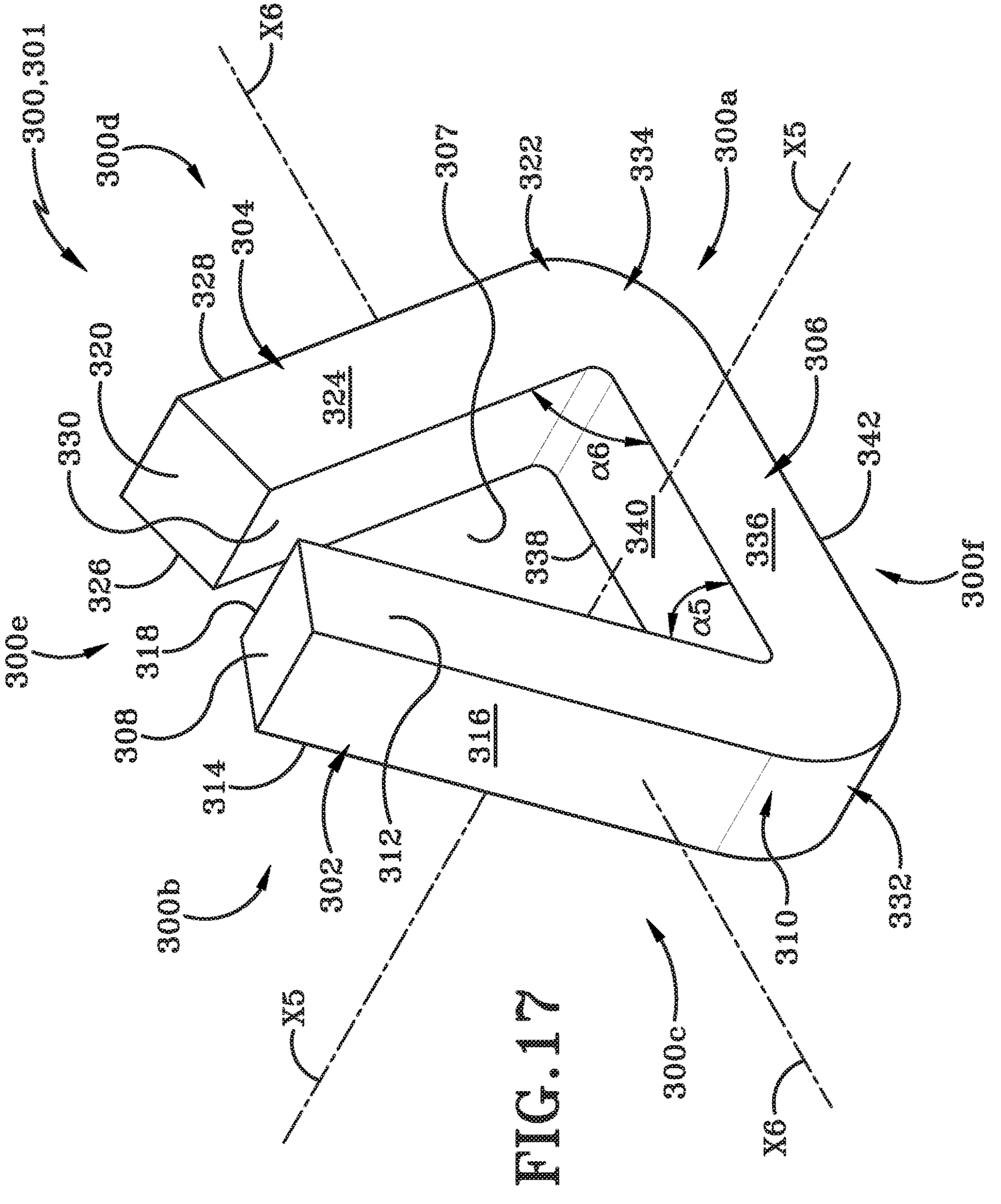
FIG. 17 is a front top side perspective view of a fourth embodiment of an airway management device in accordance with one aspect of the present disclosure.
Figure 18A:
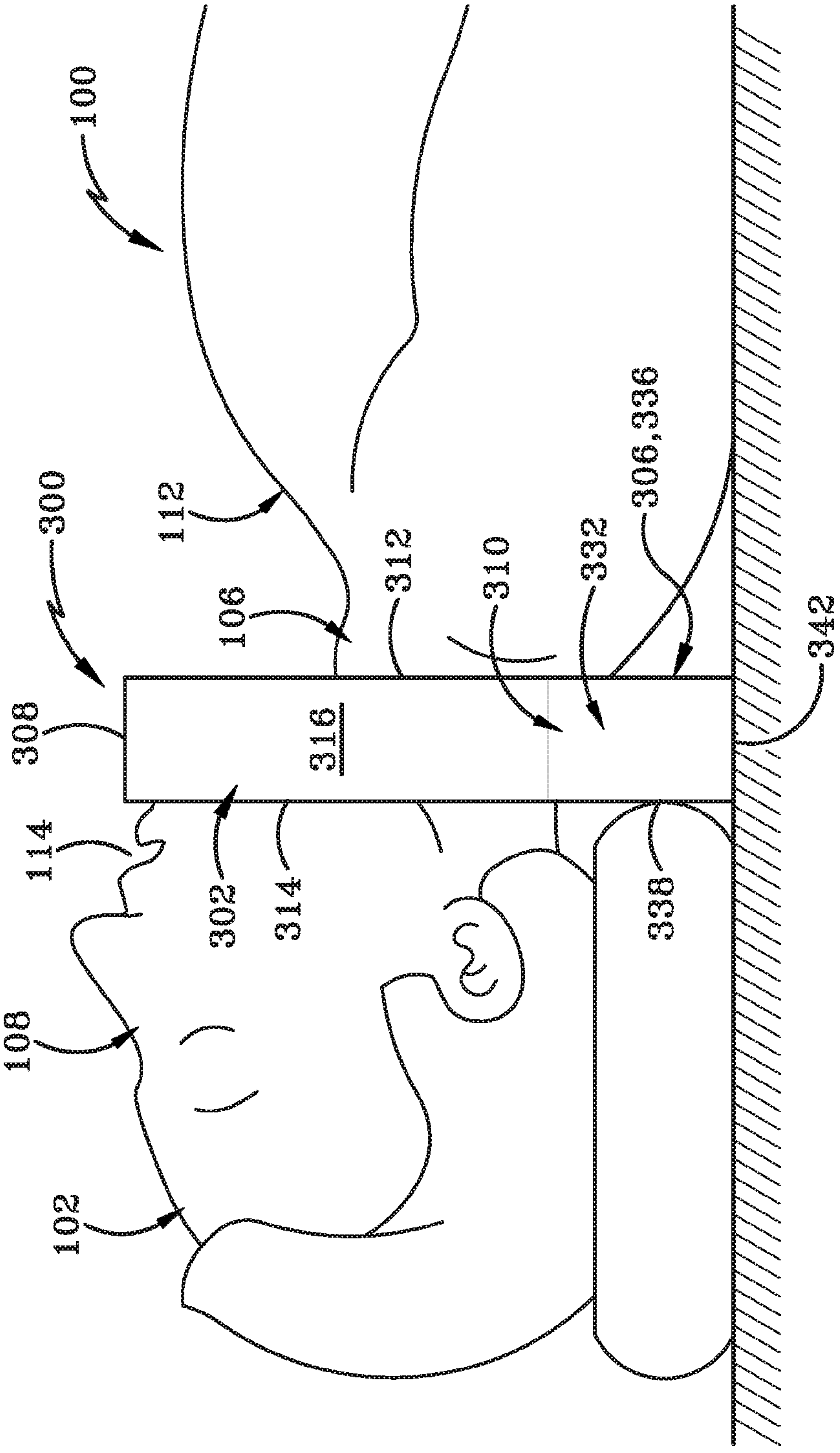
FIG. 18A is an operational view of the airway management device of FIG. 11 being utilized by a person.
Figure 18B:
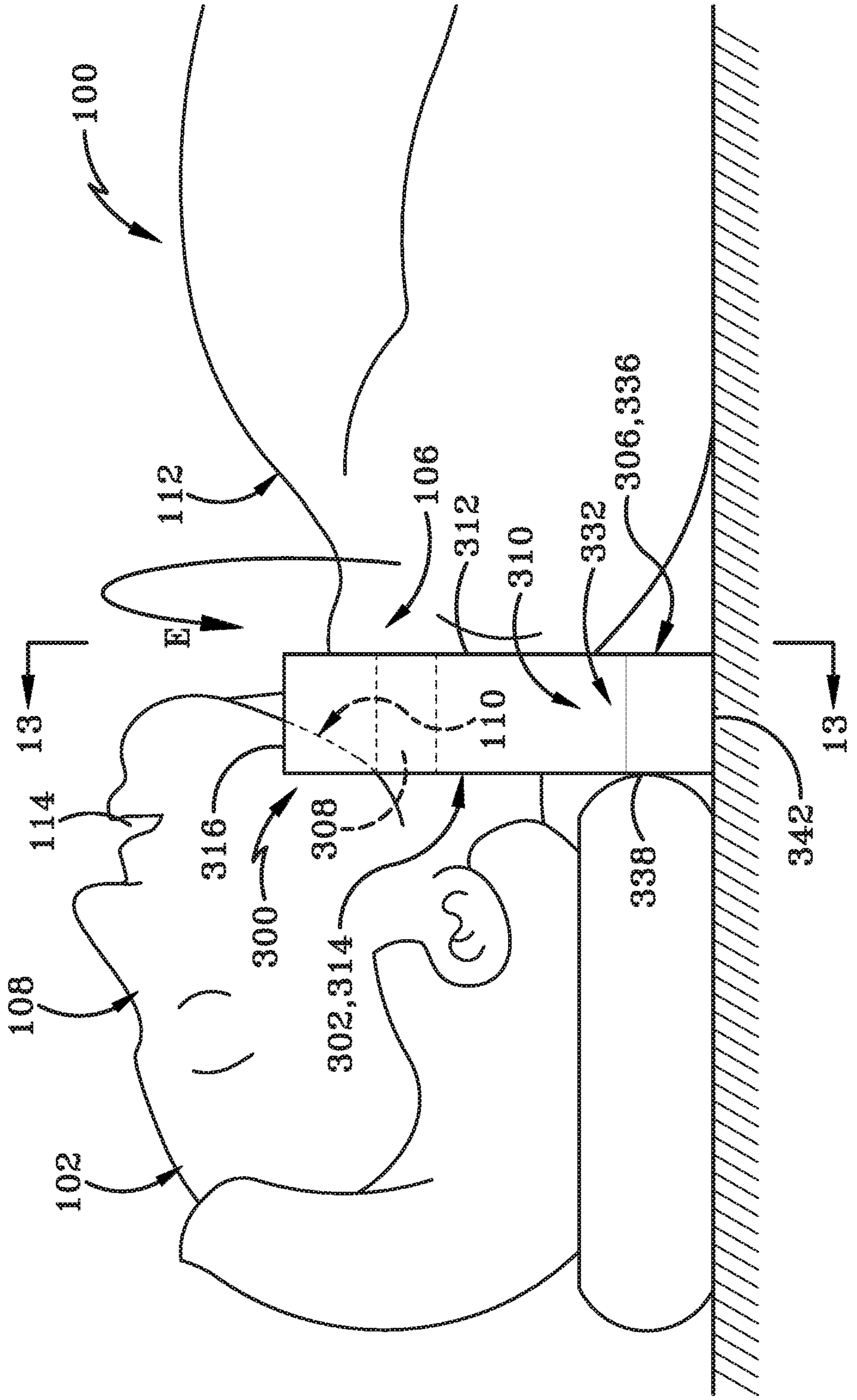
FIG. 18B is an operational view of the airway management device of FIG. 11 being utilized by the person.
Figure 19:
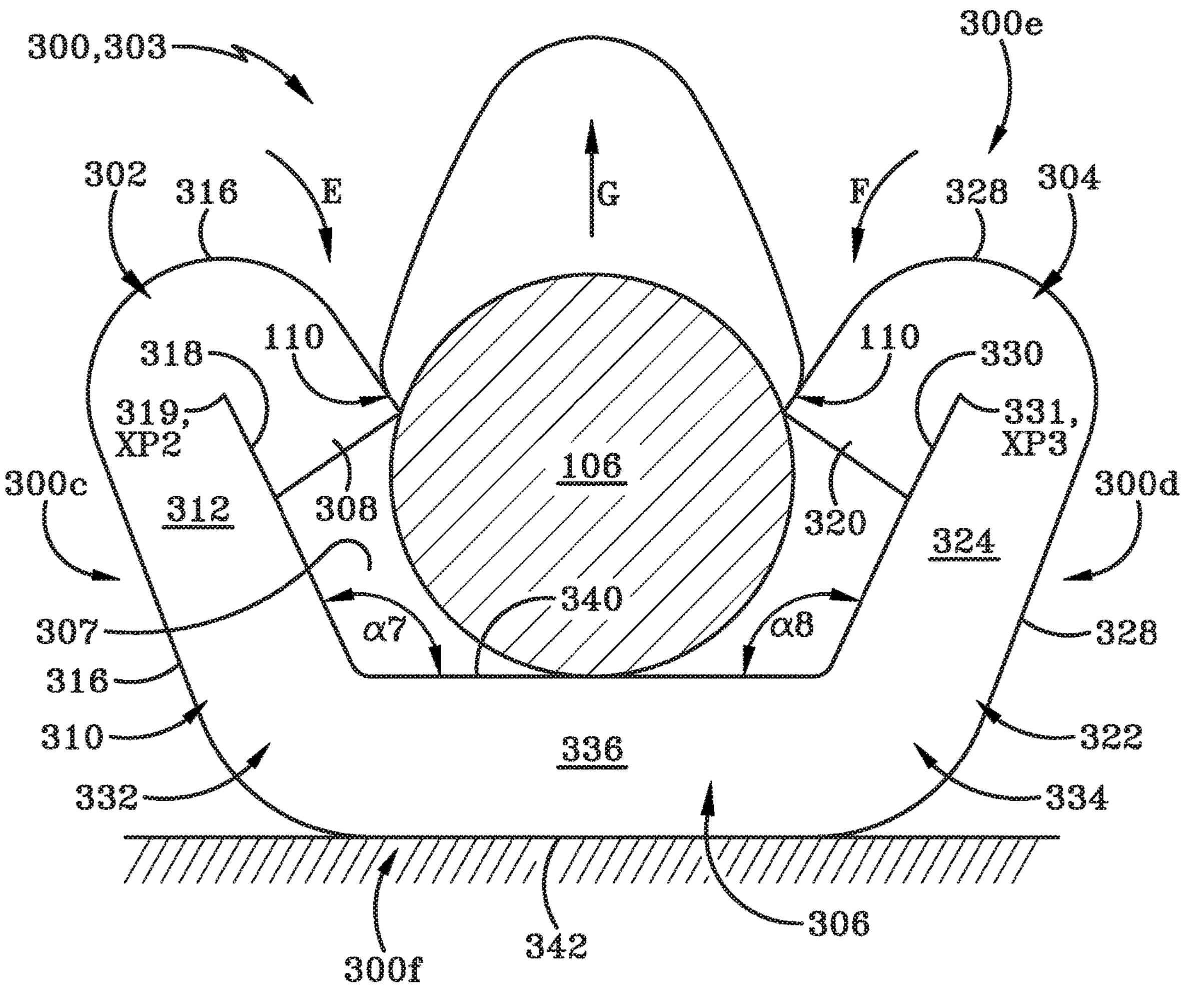
FIG. 19 is an operational view of the airway management device of FIG. 17 being utilized by a person.

Referring to FIG. 17 through FIG. 19, there is shown a fourth embodiment of an airway management device in accordance with one aspect of the present disclosure, with the airway management device generally indicated at 300. The airway management device 300 is configured to contact and provide various forces against a person's body as further described below. As such, and in one embodiment, the airway management device 300 is made out of polyurethane foam to conform to the person's body and provide comfortability while providing suitable forces against the person's body. The airway management device 300 is made out of polyurethane foam having a density of 1.8 pounds per cubic foot; however, the airway management device 300 may be made of polyurethane foam having any suitable density. It is to be further understood that the airway management device 300 may be made out of any suitable materials.

With reference to FIG. 17 through FIG. 19, the airway management device 300 is configurable between a non-deployed position 301 (FIG. 17) and a deployed position 303 (FIG. 19). When the airway management device is viewed in the neutral position 301, the airway management device 300 includes a front end **300*a* and a rear end 300*b* defining a longitudinal direction therebetween, a first side 300*c* and a second side 300*d* defining a transverse direction therebetween, and a top 300*e* and a bottom 300*f* defining a vertical direction therebetween. The airway management device 300 includes a longitudinal central axis X5 extending from the front end 300*a* to the rear end 300*b* and a transverse central axis X6 extending from the first side 300*c* to the second side 300*d***.

The airway management device 300 includes a first portion 302, a second portion 304, and a third portion 306, and an opening defined by the first portion 302, the second portion 304, and the third portion 306 as further described below. The first portion 302 includes a first end 308, a second end 310, a front wall 312, a rear wall 314, a first side wall 316, a second side wall 318, and a pivot axis XP2 defined by a pivot point 319. The second portion 304 includes a first end 320, a second end 322, a front wall 324, a rear wall 326, a first side wall 328, a second side wall 330, and a pivot axis XP3 defined by a pivot point 331. The third portion 306 includes a first end 332, a second end 334, a front wall 336, a rear wall 338, a top wall 340, and a bottom wall 342.

The second end 310 of the first portion 302 is operably engaged with the first end 332 of the third portion 306. When the airway management device 300 is in the neutral position 301, the front wall 312, the rear wall 314, the first side wall 316, and the second side wall 318 of the first portion 302 extends vertically upward at an angle α5 from the connection between the second end 310 of the first portion 302 and the first end 332 of the third portion 306 to the first end 308 of the first portion 302. In one example, the angle α5 is 70 degrees relative to the horizontal; however, the angle α5 may be any suitable angle.

The second end 322 of the second portion 304 is operably engaged with the second end 334 of the third portion 306. When the airway management device 300 is in the neutral position 301, the front wall 324, the rear wall 326, the first side wall 328, and the second side wall 330 of the second portion 304 extends vertically upward at an angle α6 from the connection between the second end 322 of the second portion 304 and the second end 334 of the third portion 306 to the first end 320 of the second portion 304. In one example, the angle α6 may be 70 degrees relative to the horizontal; however, the angle α6 may be any suitable angle.

When the airway management device 300 is in the deployed position 301, the front wall 312, the rear wall 314, the first side wall 316, and the second side wall 318 of the first portion 302 extends vertically upward at an angle α7 from the connection between the second end 310 of the first portion 302 and the first end 332 of the third portion 306 to the first end 308 of the first portion 302. In one example, the angle $\alpha$7 may be 115 degrees relative to the horizontal; however, the angle $\alpha$7 may be any suitable angle.

When the airway management device 300 is in the deployed position 301, the front wall 324, the rear wall 326, the first side wall 328, and the second side wall 330 of the second portion 304 extends vertically upward at an angle $\alpha$8 from the connection between the second end 322 of the second portion 304 and the second end 334 of the third portion 306 to the first end 320 of the second portion 304. In one example, the angle $\alpha$8 may be 115 degrees relative to the horizontal; however, the angle $\alpha$8 may be any suitable angle.

With primary reference to FIG. 18A through FIG. 19, and in operation, the airway management device 300 is utilized by a person 100 to restore and/or maintain a patent airway. As shown in FIG. 18A, when the person 100 is in the supine position, the airway management device 300 is moved from the neutral position 301 to the deployed position 302 by moving the first portion 302 and the second portion 304 in opposing directions way from the longitudinal central axis X5 to allow the person's 100 neck region 106 to be supported by the top wall 340 of the third portion 306. In operation, and as shown in FIG. 18B and FIG. 19, the first portion 302 is pivoted about the pivot axis XP2 in a direction indicated generally by arrow E such that a portion of the first end 308 and a portion of the first side wall 316 contacts the chin and posterior mandibular region 110 of the person 100, and the second portion 304 is pivoted about the pivot axis XP3 in a direction indicated generally by arrow F such that a portion of the first end 320 and a portion of the first side wall 328 contacts the chin and posterior mandibular region 110 of the person 100. The first portion 302 and the second portion 304 provide an upward force in a direction indicated generally by arrow G to the chin and posterior mandibular region 110 of the person 100. This force provides a force similar to a jaw thrust maneuver which may be defined as displacing the mandible forward which pulls the tongue forward to prevent it from obstructing the entrance to the trachea (not shown) of the person 100.

Although the airway management device 300 has been described as having various components operably engaged with one another in a particular manner, it is to be understood that some components may be integrally formed with the airway management device 300 while other components are separate from yet operably engaged with the airway management device 300. For example, and not meant as a limitation, instead of the first portion 302, the second portion 304, and the third portion 306 being integrally formed with one another, the first portion 302, the second portion 304, and the third portion 306 may be separate from yet operably engaged with one another.

In accordance with one aspect of the present disclosure, it is envisioned that the airway management devices 10, 1000, 200, and 300 may be utilized for enhancing and supporting an open airway during Monitored Anesthesia Care (MAC) anesthesia with sedation and/or regional anesthesia with sedation or any other suitable situation where a patent airway needs to be enhanced and/or maintained.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

An embodiment is an implementation or example of the present disclosure. Reference in the specification to "an embodiment," "one embodiment," "some embodiments," "one particular embodiment," or "other embodiments," or the like, means that a particular feature, structure, or characteristic described in connection with the embodiments is included in at least some embodiments, but not necessarily all embodiments, of the invention. The various appearances "an embodiment," "one embodiment," "some embodiments," "one particular embodiment," or "other embodiments," or the like, are not necessarily all referring to the same embodiments.

Additionally, any method of performing the present disclosure may occur in a sequence different than those described herein. Accordingly, no sequence of the method should be read as a limitation unless explicitly stated. It is recognizable that performing some of the steps of the method in an different order could achieve a similar result.

In the foregoing description, certain terms have been used for brevity, clearness, and understanding. No unnecessary limitations are to be implied therefrom beyond the requirement of the prior art because such terms are used for descriptive purposes and are intended to be broadly construed.

Moreover, the description and illustration of various embodiments of the disclosure are examples and the disclosure is not limited to the exact details shown or described.

The invention claimed is:

1. A method of keeping a patient's airway open comprising:

providing a base including a first base portion and a second base portion;

placing the base on a surface;

placing the patient's head on the second base portion;

pivoting the first base portion relative to the second base portion from a neutral position to a deployed position;

applying pressure to the patient's chin with the first base portion;

applying pressure to the patient's chest by detaching a pressure block extending outwardly from the first base portion from an interior aperture defined in the second base portion and operably engaging the pressure block with the first base portion; and lifting a patient's chin so that the patient's airway is unobstructed.

2. The method of claim 1, wherein the applying of pressure to the patient's chin and lifting the patient's chin is accomplished without a caregiver contacting the patient's head with their hands.

3. The method of claim 1, wherein when the first base portion is in the neutral position the first base portion and the second base portion are aligned in a same plane; and wherein when the first base portion is in the deployed position the first base portion is oriented at an angle relative to the second base portion.

4. The method of claim 3, wherein the angle is an obtuse angle.

5. The method of claim of claim 1, further comprising:

compressing the pressure block via a securing assembly.

6. The method of claim 1, wherein the pivoting of the first base portion to the deployed position further comprises:

positioning a first base arm of the first base portion on a first side of the patient's head; and positioning a second base arm of the first base portion on the other side of the patient's head.

7. The method of claim 1, further comprising:

positioning a back region of the patient's head within the aperture defined in the second base portion.

8. The method of claim 1, further comprising:

moving a region of the first base portion over a top and a front of the patient's head when moving the first base portion from the neutral position to the deployed position.

9. An apparatus for aiding in keeping a patient's airway open, said apparatus comprising:

a base including:

a first base portion;

a second base portion; and a pressure block extending outwardly from the first base portion and selectively removable from the second base portion; wherein when the pressure block is removed from the second base portion, an aperture is defined in the second base portion; and wherein the first base portion is movable relative to the second base portion between a neutral position and a deployed position; and when the first base portion is in the deployed position the first base portion is configured to lift the patient's chin and the pressure block is configured to apply pressure to the patient's chest so that the patient's airway is unobstructed.

10. The apparatus of claim 9, wherein when the first base portion is in the neutral position the first base portion and the second base portion are aligned in a same plane; and wherein when the first base portion is in the deployed position the first base portion is oriented at an angle relative to the second base portion.

11. The apparatus of claim 10, wherein the angle is an obtuse angle.

12. The apparatus of claim 10, wherein when the first base portion is in the neutral position the pressure block is oriented perpendicular to the plane.

13. The apparatus of claim of claim 9, further comprising:

a securing assembly operably engaged with the first base portion and configured to selectively compress the pressure block.

14. The apparatus of claim 13, wherein the securing assembly is a strap that is removably engaged with the first base portion.

15. The apparatus of claim 9, wherein the first base portion is substantially U-shaped in configuration and is integrally connected to the second base portion via a living hinge.

16. The apparatus of claim 15, wherein the second base portion nests inside an opening defined in the substantially U-shaped first base portion when the first base portion is in the neutral position.

* * * * *